(12) United States Patent
Flickinger

(10) Patent No.: US 8,925,544 B2
(45) Date of Patent: Jan. 6, 2015

(54) PORTABLE NEBULIZER DEVICE

(75) Inventor: William J. Flickinger, Lino Lakes, MN (US)

(73) Assignee: MedInvent, LLC, White Bear Lake, MN (US)

( * ) Notice: Subject to any disclaimer, the term of this patent is extended or adjusted under 35 U.S.C. 154(b) by 311 days.

(21) Appl. No.: 13/414,439

(22) Filed: Mar. 7, 2012

(65) Prior Publication Data

US 2012/0160237 A1    Jun. 28, 2012

Related U.S. Application Data

(63) Continuation-in-part of application No. 13/404,623, filed on Feb. 24, 2012, and a continuation-in-part of (Continued)

(51) Int. Cl.
*A61M 11/00* (2006.01)
*A61M 3/02* (2006.01)

(Continued)

(52) U.S. Cl.
CPC .............. *A61M 3/025* (2013.01); *A61M 3/0279* (2013.01); *A61M 11/06* (2013.01);

(Continued)

(58) Field of Classification Search
CPC ................ A61M 11/00; A61M 11/02; A61M 2011/006; A61M 2011/007; A61M 2011/008; A61M 15/00; A61M 15/08; A61M 16/0057; A61M 16/0066; A61M 16/0075; A61M 16/0079; A61M 16/0096; A61M 16/10; A61M 16/104; A61M 16/16; A61M 2016/12; A61M 2016/122; A61M 2016/125; A61M 2016/127; A61M 2016/14; A61M 2016/142; A61M 2016/145; A61M 2016/147; A61M 2016/16; A61M 2205/07; A61M 2205/071; A61M 2205/073; A61M 2205/075; A61M 2205/076; A61M 2205/078; A61M 16/14; A61M 2015/0005; A61M 11/06; A61M 2011/065
USPC ............ 128/200.11, 200.12, 203.16, 203.19, 128/203.22–203.24, 204.14, 204.24, 128/204.25, 207.18; 239/340, 365, 368, 239/369, 371, 372
See application file for complete search history.

(56) References Cited

U.S. PATENT DOCUMENTS 2,485,184 A    5/1948   Blackman et al.
(Continued)

FOREIGN PATENT DOCUMENTS

GB        2327223 A    1/1999
(Continued)

OTHER PUBLICATIONS

Ying, "The Nose May Help the Brain: Intranasal Drug Delivery for Treating Neurological Disease"; Future Neural, 2008, 3(1), pp. 1-4.
(Continued)

*Primary Examiner* — Justine Yu
*Assistant Examiner* — Michael Tsai
(74) *Attorney, Agent, or Firm* — Colin P. Cahoon; Celina M. Orr; Carstens & Cahoon, LLP

(57) ABSTRACT

A nasal nebulizer with a main canister for receiving fluid and an insert with a fluid channel includes a contiguous pressurized air supply source. The fluid channel may be a tapered tube overlapping an air exit port in the canister. The fluid channel may also comprise a common bell housing surrounding the air exit port above a base of the insert, which rests within the canister. The insert may include an extension projecting out to the canister and a vertical groove may extend down the fluid channel to a hole in the extension, which upon use helps create a vacuum that pulls in deflected fluid. The main canister includes a convex top surface around the periphery of an opening for a reservoir that receives fluids. The top surface extends downwardly to a generally rectangular opening that connects to the pressurized air supply source.

18 Claims, 18 Drawing Sheets

Related U.S. Application Data application No. 12/829,198, filed on Jul. 1, 2010, and a continuation-in-part of application No. 12/787,576, filed on May 26, 2010, now Pat. No. 8,146,587, which is a continuation-in-part of application No. 12/633,269, filed on Dec. 8, 2009, now Pat. No. 8,162,921.

(51) Int. Cl.
*A61M 11/06* (2006.01)
*A61M 15/08* (2006.01)
*A61M 16/00* (2006.01)

(52) U.S. Cl.
CPC ............ *A61M 15/08* (2013.01); *A61M 16/0063* (2013.01); *A61M 2205/8206* (2013.01); *A61M 2210/0618* (2013.01)
USPC ................................ 128/200.21; 128/200.14

(56) References Cited

U.S. PATENT DOCUMENTS

| | | | |
|---|---|---|---|
| 2,564,400 A | 8/1951 | Hall et al. | |
| 2,583,821 A | 1/1952 | DuBois | |
| 3,097,645 A | 7/1963 | Lester | |
| 4,093,124 A | 6/1978 | Morane et al. | |
| 4,251,033 A * | 2/1981 | Rich et al. | 239/338 |
| 4,657,007 A | 4/1987 | Carlin et al. | |
| 5,224,471 A | 7/1993 | Marelli et al. | |
| 5,549,102 A * | 8/1996 | Lintl et al. | 128/200.21 |
| 5,579,757 A | 12/1996 | McMahon et al. | |
| 5,584,285 A | 12/1996 | Salter et al. | |
| 5,624,898 A | 4/1997 | Frey, II | |
| 5,653,223 A | 8/1997 | Pruitt | |
| 5,806,723 A | 9/1998 | DuBose | |
| 5,906,198 A | 5/1999 | Flickinger | |
| 6,313,093 B1 | 11/2001 | Frey, II | |
| 6,619,284 B2 | 9/2003 | Kong | |
| 6,644,304 B2 | 11/2003 | Grychowski et al. | |
| 6,644,305 B2 | 11/2003 | MacRae et al. | |
| 6,698,421 B2 * | 3/2004 | Attolini | 128/200.14 |
| 6,732,731 B1 | 5/2004 | Tseng | |
| 7,131,439 B2 * | 11/2006 | Blacker et al. | 128/200.18 |
| 7,288,083 B2 | 10/2007 | Holman | |
| 7,407,118 B2 | 8/2008 | Sevy | |
| 7,559,491 B1 | 7/2009 | Chang | |
| 8,616,195 B2 | 12/2013 | Power et al. | |
| 2004/0031485 A1 | 2/2004 | Rustad et al. | |
| 2008/0054099 A1 | 3/2008 | Giroux et al. | |
| 2011/0137290 A1 | 6/2011 | Flickinger et al. | |
| 2011/0303218 A1 | 12/2011 | Yadidi | |
| 2012/0000460 A1 | 1/2012 | Flickinger | |
| 2012/0152238 A1 | 6/2012 | Flickinger | |

FOREIGN PATENT DOCUMENTS

| | | |
|---|---|---|
| TW | 200932204 A | 8/2009 |
| WO | 0189615 A1 | 11/2001 |
| WO | 20111153406 A2 | 12/2011 |

OTHER PUBLICATIONS

Manes, R. Peter et al. "Prospective Evaluation of Aerosol Delivery by a Powered Nasal Nebulizer in the Cadaver Model" International Forum of Allergy & Rhinology, vol. 1, No. 5, Sep./Oct. 2011, pp. 366-371.

* cited by examiner

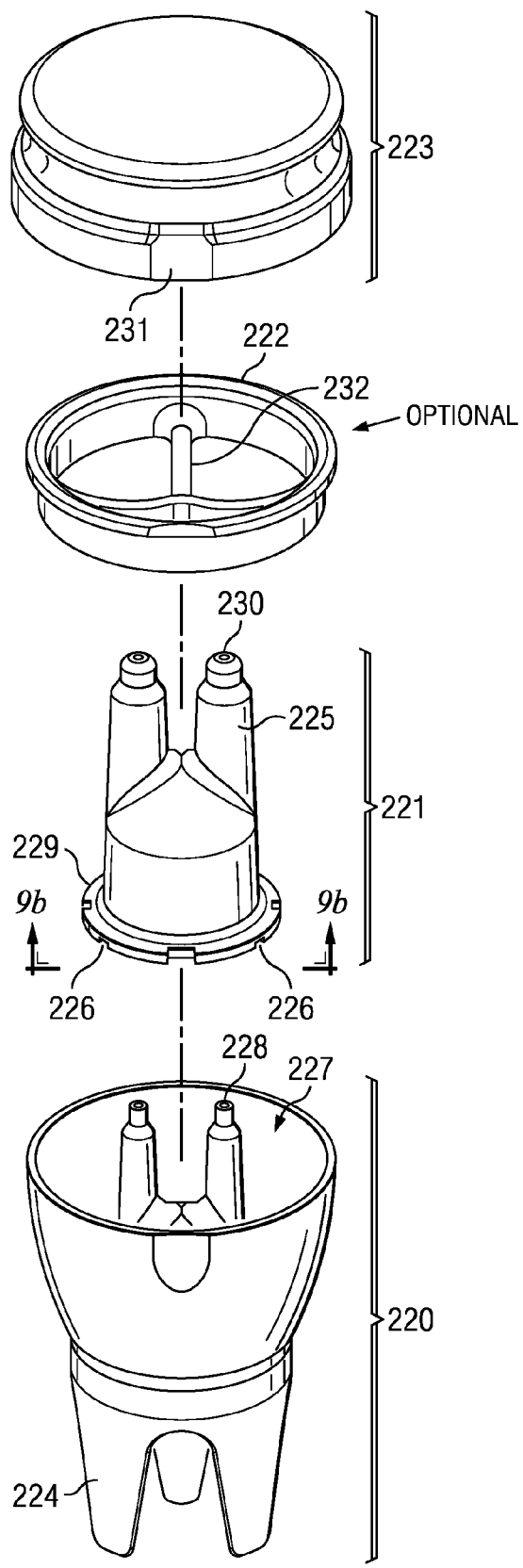
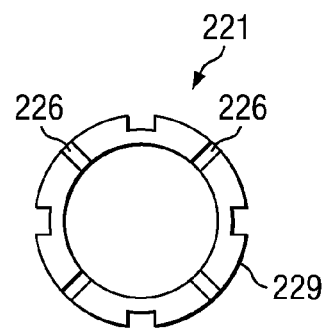
*FIG. 9b*
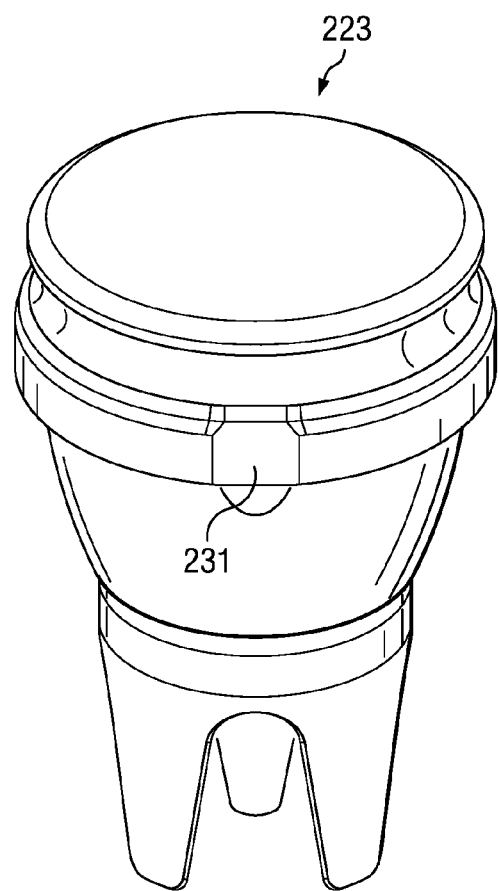
*FIG. 10*
*FIG. 9a*

PORTABLE NEBULIZER DEVICE

CROSS-REFERENCE TO RELATED APPLICATIONS

This application is a continuation-in-part of and claims filing priority rights with respect to currently pending U.S. patent application Ser. No. 12/633,269 filed Dec. 8, 2009, which published on Jun. 9, 2011, as U.S. Publication No. 2011/0137290; Ser. No. 12/787,576 filed May 26, 2010, which published on Jun. 9, 2011, as U.S. Publication No. 2011/0132354; Ser. No. 12/829,198 filed Jul. 1, 2010, which was published Jan. 5, 2012, as U.S. Publication 2012/0000460; and Ser. No. 13/404,623 filed Feb. 24, 2012. The technical disclosures of all of the above-mentioned applications are hereby incorporated herein by reference.

TECHNICAL FIELD

The present invention generally relates to devices used for administering fluid to the upper airway in mist or droplet form, either for the irrigation of the nasal passages or the delivery of medication in a nasal nebulizer.

BACKGROUND OF THE INVENTION

Devices used for administering liquid medication to a patient by way of mist or liquid droplets are generally called nebulizers and are primarily used for the delivery of medication into the lungs. These devices are best suited for the inhalation of the liquid droplets through the patient's mouth. However, some cases require the introduction of liquid droplets to the patient's nasal passages.

Current nebulizers for introduction of medication to or irrigation of the nasal passages generally comprise an air compressor, a nebulizer cup for medication, and compressor tubing to connect the compressor to the nebulizer cup. To use the nebulizer, the compressor must be placed on a sturdy surface in order to support its weight and its power supply cord must be plugged into an outlet. In general, the compressor is not a portable or lightweight device. Thus, it is the compressor tubing that provides for a convenient way of handling the nebulizer cup during use.

It would be desirable to have a nebulizer that allows for more convenient use not requiring connecting tubing, a power supply cord, or a heavy or bulky compressor. Such nebulizer should, as a whole, be lightweight and easy to handle. In addition, such a nebulizer should be small enough to be carried or moved with ease to provide for convenience while still having the power to reach the desired areas of the nasal passage. Finally, it would be desirable to have a portable nebulizer that can be readily used at any time without having to search for a nearby electrical outlet.

SUMMARY OF THE INVENTION

The present invention generally provides a portable, ready-to-use device for nasal irrigation and drug delivery wherein fluid held in a canister is atomized via a contiguously attached compressed air supply to create particles sized for dispersion and retention within the nasal cavity delivered via a pressurized flow that is able to stent-open the soft tissues of the nose to deliver the resultant mist into the whole of the nasal passages without the need for the patient to create an airstream through inhalation. More specifically, the present invention comprises a nebulizer device that comprises a main canister section, an insert, removable cap, and a contiguous pressurized air supply directly and immediately connected to the main canister section. The nebulizer device requires no connecting tubing or power cord. Instead, the pressurized air supply forms a part of the handheld portion of the nebulizer device. Preferably, the pressurized air supply comprises an air compressor.

The main canister section comprises at least one air exit port and an air inlet, through which compressed air is introduced. The insert sits within a reservoir of the canister and comprises a fluid channel that fits over the air exit port, providing a small space between the outer surface of the air exit port and the inner surface of the fluid channel. The main canister comprises a convexly curved top portion extending down into a generally rectangular bottom opening that mates with a pressurized air supply source. When pressurized air is introduced by the handheld air compressor through the air inlet of the main canister, fluid is drawn between the air exit port and fluid channel due to a venturi effect created, thereby expelling the fluid medication as mist through an exit hole in the fluid channel.

Other aspects, embodiments and features of the invention will become apparent from the following detailed description of the invention when considered in conjunction with the accompanying drawings. The accompanying drawings are schematic and not intended to be drawn to scale. In the figures, each identical or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF THE DRAWINGS

The novel features believed characteristic of the invention are set forth in the appended claims. The invention itself, however, as well as mode of use and advantages thereof, will best be understood by reference to the following detailed description of illustrative embodiments when read in conjunction with the accompanying drawings, wherein:

FIG. 9*a* shows an exploded view of an embodiment of a nasal nebulizer in accordance with an embodiment of the present invention.

FIG. 9*b* shows a bottom view of an insert in accordance with an embodiment of the present invention.

FIG. 10 shows a perspective view of an assembled nasal nebulizer in accordance with an embodiment of the present invention.

DETAILED DESCRIPTION

The present invention improves upon current nebulizer designs and provides a method of delivering fluid to the nasal passages with little interaction required by the user, under sufficient pressure to stent-open the airway, and with particles of a size to ensure that the majority of the mist is retained or deposited within the upper airway. The invention also provides a nasal nebulizer designed to deliver a mist to the upper airway through both nostrils simultaneously.

In one aspect, a nasal nebulizer of the present invention comprises a main canister with a reservoir for holding fluid, wherein the canister includes at least two air exit ports; a removable insert with a circular base that fits within said main canister, wherein the insert includes at least two fluid channels that mate with said air exit ports of the main canister, said fluid channels comprising two tubes ending in a common bell housing above the base, wherein said base holds the insert just off of the main canister surface, allowing fluid to pass between the base and main canister, and further wherein the fluid channels are larger in diameter than the air exit ports, thereby providing a small space between the outer surface of the air exit ports and the inner surface of the fluid channels that allows fluid from said reservoir to be drawn upward between the air exit ports and fluid channels and expelled as a mist in an aerosol plume through exit holes in the fluid channels due to a venturi effect created by pressurized air from the air exit ports; and at least one nozzle coupled to the bottom of said main canister to create at least one air chamber defined by the nozzle and said air exit ports, wherein the nozzle includes an air inlet for providing pressurized air into said air chamber.

Figure 1:
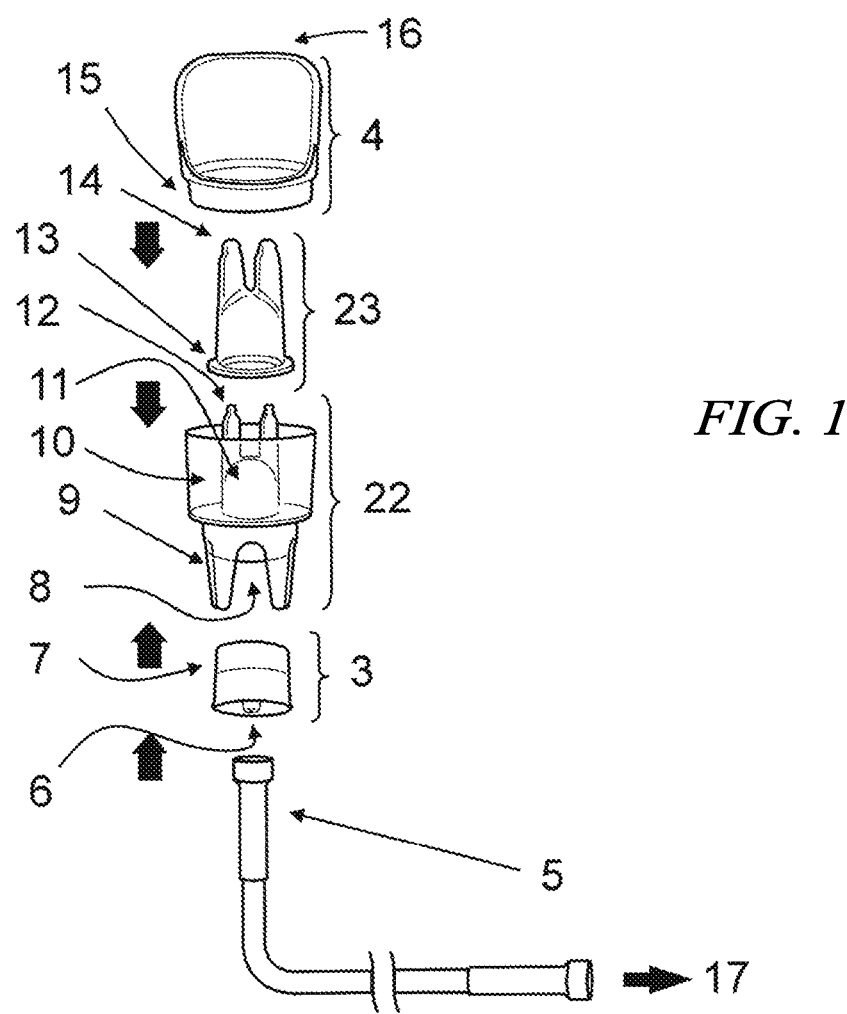
FIG. 1 is an exploded view of a nasal nebulizer in accordance with an embodiment of the present invention.

FIG. 1 is an exploded view of a nasal nebulizer in accordance with an embodiment of the present invention. The nasal irrigation device comprises three major sections. The first major section is the main canister 22 which has an expanded reservoir 10 that is capable of holding up to 50 ml of fluid. The inner portion of the reservoir shaped at the bottom to ensure maximal uptake of fluid to reduce waste.

The main canister 22 also includes an air chamber 11 terminating in two air exits 12 (one for each nostril) with holes sufficient to deliver an airstream that is able to atomize fluid and stent-open the upper airway. In one embodiment, each exit port 12 has at least one hole of between 0.020" and 0.060" (0.508 mm-1.524 mm) in diameter and a web-thickness or hole length of between 0.030" and 0.200" (0.762 mm-5.08 mm).

On the bottom of the main canister 22 is a foot section 9 that includes one or more feet for stability and an air inlet 8 for the admission of pressurized air to create the air stream through air exits 12. The foot section 9 enables the canister 22 to stand up when set on a horizontal surface and is designed to fit into a standard docking port of an air compressor pump to enable the device to remain upright in a hands-free manner so as to remain filled with the air supply tube attached.

In the shown example, the main canister 22 has a two-step circumference to fit a holder (not shown) and provide adequate fluid volume for nasal irrigation, with the smaller diameter foot section 9 enabling the user to rest device in the holder with tube attached. In an alternate embodiment (not shown) the foot section 9 is wider than the reservoir section 10.

The second major section of the nebulizer is the insert 23, which is shown with a base 13 that holds the inside surface of the insert 23 just off of the outer surface of the feature within reservoir 10 of the main canister 22. At least one channel is located in the bottom of the insert 23 to act as a conduit for fluid from the reservoir 10 to enter the base of the insert. The insert 23 includes fluid channels 14 that mate with the air exit ports 12 of the main canister 22. Peaks or extensions may be included on the air exits 12 to ensure centering of the insert 23 and its fluid channels 14 on the air exits. Similarly, tabs may extend from the inside of the fluid channels of the insert to the outer surface of the main canister to ensure alignment. As shown, fluid channels 14 of the insert 23 comprise two tubes with one end at the bottom of the reservoir 10 and one end that is positioned in the airstream so that the airstream creates a negative pressure in each tube that draws fluid into the airstream where it is atomized (described below).

In the embodiment shown in FIG. 1, the atomizer outlets 12, 14 extend above the edge of the main canister 22. However, in an alternate embodiment (not shown) the atomizer nozzles are even with or recessed within the edge or portions of the edge of the main canister.

The insert 23 is keyed in at least one location with the reservoir 10 to ensure that the insert does not rotate in relation to the exit ports 12 of the main canister and to aid in centering of the insert 23 and its fluid channels 14 on the air exits. The insert may include a feature to ensure that it is inserted into the main canister in only one orientation. In one embodiment, a loop (not shown) extends down to the saddle of the insert 23 to hold down the insert.

The fluid channels 14 are slightly larger in diameter than the air exit ports 12 of the main canister, thereby providing a small space (preferably 0.0001" to 0.010" (0.00254-0.254 mm)) between the outer surface of the air exit ports and the inner surface of the fluid channels. This space allows fluid from the reservoir 10 to proceed upward between the air exit ports 12 and the fluid channels 14 until being expelled by pressurized air. When the insert 23 is installed in the main canister 22, the orifices of the fluid channels 14 are positioned relative to the air exits 12 so as to create a venturi effect with the pressurized gas expelled from the gas tubes. Because the fluid exits 14 in the insert 23 are larger than the air exits 12, when air is forced through the air exits at an appropriate volume and speed, fluid in the reservoir 10 is drawn up into the space between the insert and air exits ports. When this fluid meets the subsequent airstream it is atomized into particles conducive to deposition in the upper airway. The airstream is sufficient to penetrate the nasal cavity above the inferior turbinate so as to deposit the fluid and provide a washing, irrigation, or deposition to the upper reaches the nasal cavity.

The exit holes of the fluid channels 14 are small enough to ensure that mist is created but large enough to ensure that the holes of the insert may be chamfered so that the walls of the exit holes are angled away from a central axis at an angle that exceeds the cone of the aerosol plume to reduce agglomeration of the mist particles upon exit, providing a more uniform particle size throughout the plume. The fluid channel size may be adjusted to change the particle size of the mist. In one embodiment the tubes have a mating section on the upper end that enables the changing of the orifice in the air stream via a series of nozzles that can be inserted into the upper end of the tubes such that the size of the nozzle orifice that is placed into the airstream is varied.

The third major section of the nebulizer is nozzle cone 3. The nozzle 3 includes an air inlet 6 and a mating surface 7, which attaches to the air inlet 8 of the main canister 22 to create air chamber 11 defined by the nozzle and the two exit ports 12 described above. The length of all components on the nozzle cone 3 preferably is limited so that the nozzle cone or its components do not extend past the foot section 9 on the main canister 22 when the device is assembled to enable the device to be placed on a flat surface in an upright or standing position.

Ribs may also be molded into the nozzle cone 3 to provide radial stiffness. In another embodiment, the nozzle cone is made of rigid plastic.

The mating surface between the nozzle 3 and main canister 22 is designed to ensure a tight bond can be created. In an alternate embodiment the mating surface between the nozzle 3 and main canister 22 is essentially straight.

In one embodiment, the nozzle cone 3 is attached permanently to the main canister 22. In an alternate embodiment, the nozzle cone 3 may utilize a friction fit or have a positive connection such as a thread or other mechanism allowing the nozzle cone and main canister 22 to be disconnected for cleaning. This detachable embodiment may include an air seal such as an O-ring as well as a flange to grasp for easy disassembly.

An air supply tube 5 connects the air inlet 6 of the nozzle cone with an air supply 17.

Figure 2:
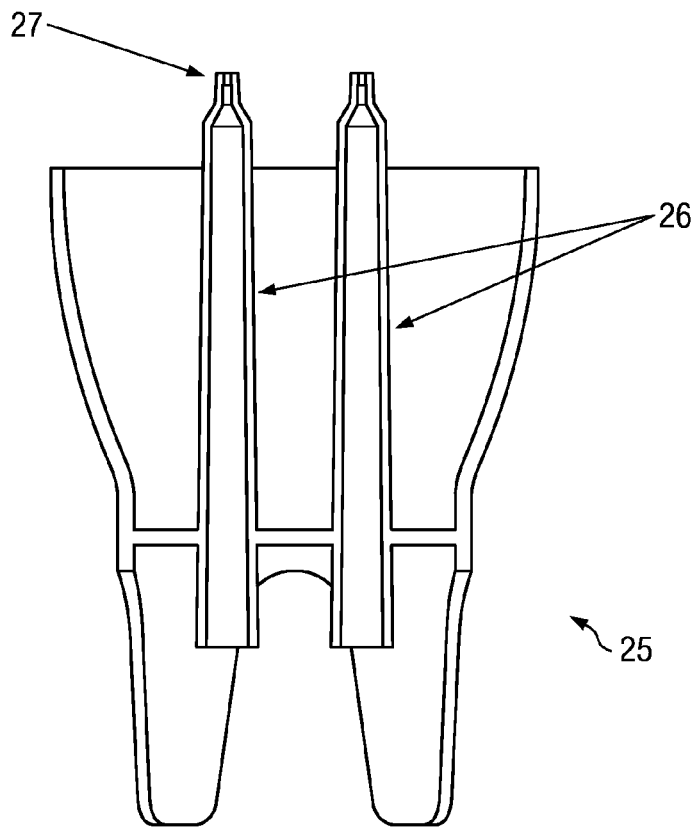
FIG. 2 shows a cross sectional view of a canister in accordance with an alternate embodiment of the invention.

FIG. 2 shows a cross section view of a canister 25 in accordance with an alternate embodiment of the invention. In this embodiment, rather than a single air chamber and nozzle, the canister 25 includes separate air passage chambers 26 that terminate in the air exits 27. These separate air passage chambers 26 can connect to separate air sources via separate nozzles. Alternatively, the separate air passage chambers 26 can be connected to a common air source via split tubing such as a Y or T adapter (not shown).

In addition to the three major sections described above, the nebulizer may include a cover 4 which has a mating surface 15 that creates an isodiametric connection to the main canister 22. In the example shown in FIG. 1, the cover 4 is a broad cover region to block space between the nose, eyes and the rest of the face when in use as shown (see FIG. 4). In this embodiment the cover 4 is designed to confine the mist expelled from the fluid channels and shield the patient's eyes, with an opening to provide room for the patient's nose within the apparatus. The cover 4 is radiused along the distal end away from the main canister 22 to fit a broad variety of faces and is open to enable air to enter as the fluid is drawn down and capture and recycle fluid that falls off the face.

The cover may also incorporate a cross member or other device that retains the insert 23 to allow for clearance of the nose and prevent lifting of the insert at the initiation of atomization. In one embodiment a sleeve or partial sleeve extends from the cover 4 to the base of the insert 23 to hold the insert down.

Figure 3:
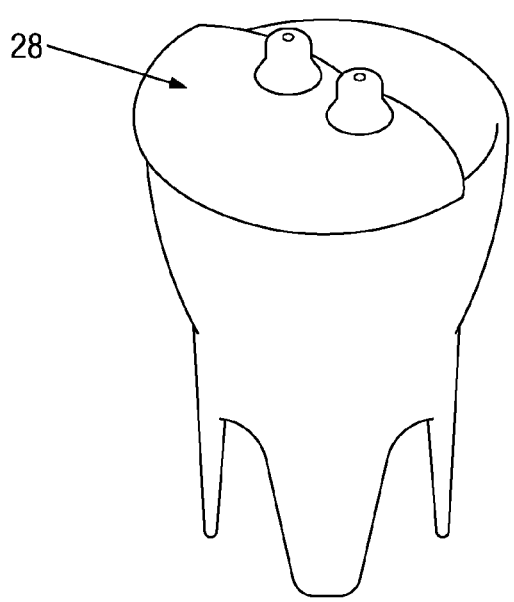
FIG. 3 shows an alternate embodiment of the cover in accordance with the present invention.

FIG. 3 shows an alternate embodiment of the cover in accordance with the present invention. In this embodiment, the cover 28 is a semi-circular lid that does not block the eyes but instead retains the insert and blocks material from re-entering the main canister from the nose.

The present invention may incorporate a feature that guides the user to angle the spray into the nose at a set angle from 0-90 degrees from the plane defined as the front of the face from the chin to the forehead (i.e. the vertical plane of the face). For example, the nebulizer may include a setoff designed to set a specific angle of 30 degrees, 45 degrees, or 60 degrees from the vertical plane of the face. The setoff may be removable for various size faces or noses.

Materials suitable for construction of the nebulizer include rigid plastic, glass, metal, ceramic, carbon fiber or other rigid material, or an elastomer plastic or some combination thereof.

One embodiment of the nasal irrigation device (not shown) is egg-shaped or ovoid for better fit into the hand and a pleasing look.

Figure 4:
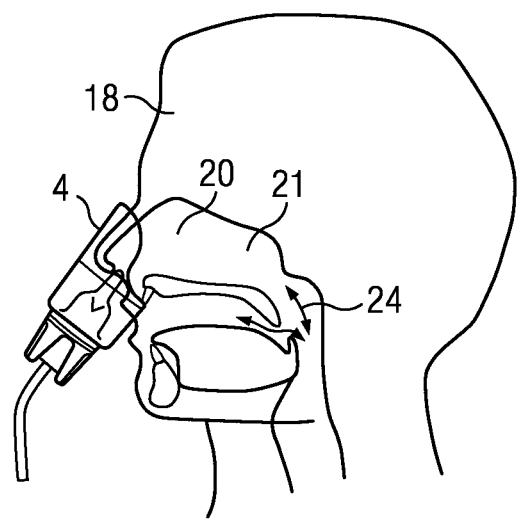
FIG. 4 illustrates the use of the nasal nebulizer of FIG. 1 in accordance with an embodiment of the present invention.

FIG. 4 illustrates the use of the nasal nebulizer in accordance with the present invention. The nebulizer is placed over the face of the user 18 and angled such that the cover 4 blocks the eyes. The mist 20 enters the nasal passages 21, and the patient breathes through both the mouth and nose at the same time (24). The mist 20 passes into the nasal passages 21 independent of the patient's breathing.

The air-fluid mixture is calibrated to achieve nasal irrigation within a short period of time, without the need for the fluid to exit the nostrils at the time of irrigation, and with a particle size that is designed to loosen the mucous or to enter the sinus cavities, as desired by the end user and not enter the pharynx or the lungs.

In one aspect, the method of nasal irrigation comprises providing fluid in a canister that includes at least two air exit ports mated to corresponding fluid channels, wherein the fluid channels are larger in diameter than the air exit ports, thereby providing a small space between the outer surface of the air exit ports and the inner surface of the fluid channels. This space allows fluid from said reservoir to be drawn upward between the air exit ports and fluid channels. Pressurized air is pumped through the air exit ports, thereby creating a venturi effect that draws fluid from said reservoir upward between the air exit ports and fluid channels and expels the fluid as a mist in an aerosol plume through exit holes in the fluid channels and into a user's nasal cavity above the inferior nasal turbinate independent of the user's breathing. The pressurized air has a pressure of 0.069-1.035 bar and an airflow rate of 1-12 liters per minute, producing a fluid delivery rate of 1-20 ml per minute.

The method of nasal irrigation offers a fast, convenient method of atomizing saline or medication for delivery to the nose, with a variable particle size up to 100 microns. In one embodiment, particle size is at least 10 microns.

Using an air pressure of 1-15 psi (0.069-1.035 bar) creates a pressurized airflow that enables the resultant air-mist stream to stent-open the soft tissues of the upper airway. Optimal performance appears to occur at 3-12 psi (0.207-0.823 bar), 1-12 lpm of airflow, and a fluid delivery rate of 1-20 ml per minute but will vary according to the needs of the patient. Typical performance is 4-8 psi (0.276-0.552 bar) pressure, 3.5-8 lpm airflow, and 15 ml per minute fluid delivery.

The resultant mist reaches the area of the nasal cavity and paranasal sinuses above the inferior nasal turbinate or chonchae to ensure that the mist reaches the areas of the sinus ostia to clear this area of the nasal cavity and enable the natural mucociliary flow to clear the sinuses.

Recent medical research has noted that the olfactory and trigeminal nerves may be used as a pathway to deliver large and small molecules to the brain and central nervous system that bypasses the blood brain barrier and first pass metabolism of intravenous and oral delivery routes. (See Dhanda, D., Frey W H $2^{nd}$, Leopold, D., Kompella, U B: "Nose-to-brain delivery approaches for drug deposition in the human olfactory epithelium." *Drug Delivery Technol.* 5(4), 64-72 (2005).) Frey and others have demonstrated that these nerves may be reached via the nasal mucosa overlying the olfactory cleft and cribriform plate where these nerves are concentrated. Furthermore, the frequency of dosing of many of these materials requires a delivery system that is practical and easy to use. In the case where systemic delivery of drugs via the nose is desired, maximizing the surface area of the mucosa covered by the medication may improve the amount of medication that is absorbed by the body and may reduce the variability of absorption between doses and across patients; thus improving the bioavailability of the drug and reducing the variability of bioavailability of the drug. Furthermore, by maximizing the surface area available for absorption of any given drug, the concentration required to deliver an effective dose may be reduced when compared to traditional metered dose inhaler technology, enabling more drugs to be delivered transnasally than with other systems.

However, the literature suggests that adequate delivery systems are lacking for the reliable and practical delivery of these substances to these areas. Delivery of large particles (>10 microns) of liquids in the described volumes as provided by the present invention, offers advantages over dry powder, minute volumes and high volume solutions. These advantages include covering the whole nasal mucosa, formulating drugs for patient comfort vs. concentration, reducing the inadvertent delivery of aerosolized materials to the lungs; and the ability to deliver precious materials economically and judiciously while reducing waste.

In one aspect, the present invention provides a method of treating neoplasms of the nasal cavity comprising fluid in a canister, wherein the canister includes a reservoir and at least two air exit ports, and wherein said fluid contains corticosteroids. The air exit ports are mated to corresponding fluid channels, wherein the fluid channels are larger in diameter than the air exit ports, thereby providing a space between the outer surface of the air exit ports and the inner surface of the fluid channels, which allows fluid from said reservoir to be drawn upward between the air exit ports and fluid channels. Pressurized air is pumped through the air exit ports, thereby creating a venturi effect that draws fluid from said reservoir upward between the air exit ports and fluid channels and expels the fluid as a mist in an aerosol plume through exit holes in the fluid channels and into a user's nasal cavity above the inferior nasal turbinate independent of the user's breathing.

The present invention allows for delivering steroids for the long-term control of benign neoplasms of the nasal cavity, such as inflammatory nasal polyps, granulomas, etc., without systemic doses of steroids or steroid injections. It also provides the ability to irrigate the whole nasal mucosa to manage the disruption of natural filtering and humidification often caused by ablative and reconstructive surgical treatment of neoplasms. Unlike prior art saline irrigation and nasal sprays which do not reach many of the areas of concern in the nasal vestibule and paranasal sinus areas, the nebulizer of the present invention delivers adequate moisture in less than one minute to the areas of concern. The present invention also avoids pooling of moisture that can otherwise provide a nidus for infection and cause excessive removal of the immunologic mucus blanket of the nose.

The high frequency of steroid administration needed to control neoplasm growth requires a delivery system that is practical and easy to use. The nebulizer of the present invention can deliver these steroids quickly—in less than one minute—covering the whole nasal cavity and does so without unduly exposing the body to the effects of systemic steroids.

For example, using the nebulizer of the present invention, 0.60 mgs of corticosteroid is typically delivered to the nasal cavity, between two and ten times the amount delivered via metered dose inhalers. In some instances, antibiotics are delivered along with the corticosteroid to treat infections such as Staphylococcus aureus. Staph aureus endotoxin has been shown to up-regulate the beta isoform of cortisol receptor ($CR_\beta$) in cell membranes that is responsible for inhibiting the response to corticosteroids, and it is believed that the Staph infection may contribute to steroid-resistant nasal polyps. The concurrent administration of antibiotics with the corticosteroid via the nebulizer of the present invention reduces this endotoxin effect on the cortisol receptor, thereby increasing the efficacy of the steroid therapy.

The pressure and airflow necessary to deliver material to the upper portion of the nose can be reduced if the aerosol is introduced distal of the nares at or above the nasal valve and proximal to the inferior turbinate. The present invention delivers droplets or mists with an air stream and particle sizes designed to stay in the upper airway under sufficient pressure and airflow to overcome the normal aerodynamics of the nose. Unlike prior art methods, the present invention releases mist at or above the nasal valve, thereby avoiding deflection of the fluid off the walls of the nostril and nasal valve.

Effective delivery of material to the nasal cavity requires a particle size that is large enough to fall out of the airway before reaching the oropharynx, delivered under sufficient pressure and airflow to overcome the aerodynamics of the nasal cavity. The nasal cavity is shaped to efficiently deliver air to the lungs. Air enters the nares and passes through the nasal valve, which resides approximately 1.3 cm above the nares and is the narrowest portion of the nose, with a cross-section of at approximately 0.73 $cm^2$. The nasal valve is the narrowest anatomic portion of the upper airway, resulting in the volume of air inspired nasally to be efficiently cleansed and humidified by the nasal cavity.

Figure 5:
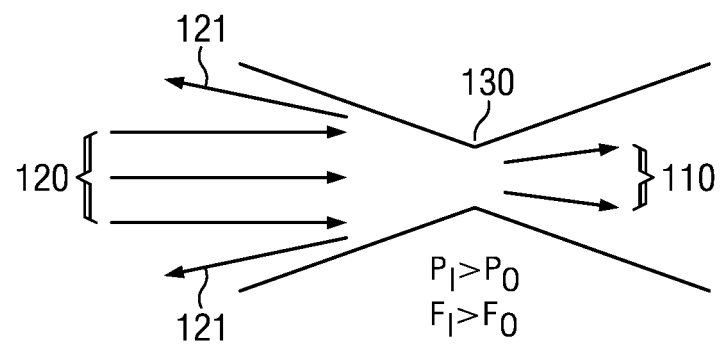
FIG. 5 conceptually illustrates the function of the nasal valve in aerosol delivery that is initiated below the nasal valve.

FIG. 5 conceptually illustrates the function of the nasal valve in aerosol delivery that is initiated below the nasal valve. Arrows 120 represent an aerosol flowing into the nasal nares. As illustrated by arrows 121, a portion of this aerosol is reflected off the walls of the nose as the passageway narrows to the nasal valve 130. This reflected material falls out of the nose and is either wasted or is recollected by the device to be delivered repeatedly.

The nasal valve 130 acts to reduce the flow (F) and pressure (P) of that portion of the aerosol stream that crosses the valve and enters the nasal cavity 110. Thus, Flow in ($F_I$) is greater than Flow out ($F_O$), and Pressure in ($P_I$) is greater than Pressure out ($P_O$). As a result, aerosol entering the nasal cavity external to the nasal valve requires a higher pressure and flow rate to achieve the same aerosol distribution as an aerosol introduced internal to the nasal valve.

Air entering the nose meets additional resistance at the level of the inferior turbinate, which directs air downward along the floor of the nose along the path of least resistance. During inhalation, the airflow is dominated by the negative pressure being generated from the lower airway and is directed to the nose from the pharynx. This negative pressure and the structure of the nasal cavity conspire to direct the majority of the air through the lower third of the nose, with very little air entering the upper portion of the nose. Indeed, studies have shown that to reach the upper portion of the nose under the negative pressure of normal breathing, an aerosol must be placed very precisely at the front of the nares. To overcome the aerodynamics of the nose, the delivery system must provide a positive pressure and sufficient airflow to fill the whole nasal cavity.

Prior art devices that deliver aerosol below the nasal valve must generate higher pressure and flow rates since the valve acts to lower the pressure and flow as the aerosol passes through it. The design of the present invention is directed to the self-administration of fluid to the nasal passages of a patient while ensuring the device fits a wide variety of faces and for simplicity of design, ease of manufacturer. It requires lower pressure and airflow and produces less mess by virtue of delivery above the nasal valve, and simplicity of use, including short delivery times.

The invention delivers fluid to the nasal passages with little interaction required by the user and under sufficient pressure to stent-open the airway. The invention delivers particles of a size to ensure that the majority of the mist is retained or deposited within the upper airway, while maximizing the amount of drug delivered and eliminating reflection back from the nasal valve.

Figure 6:
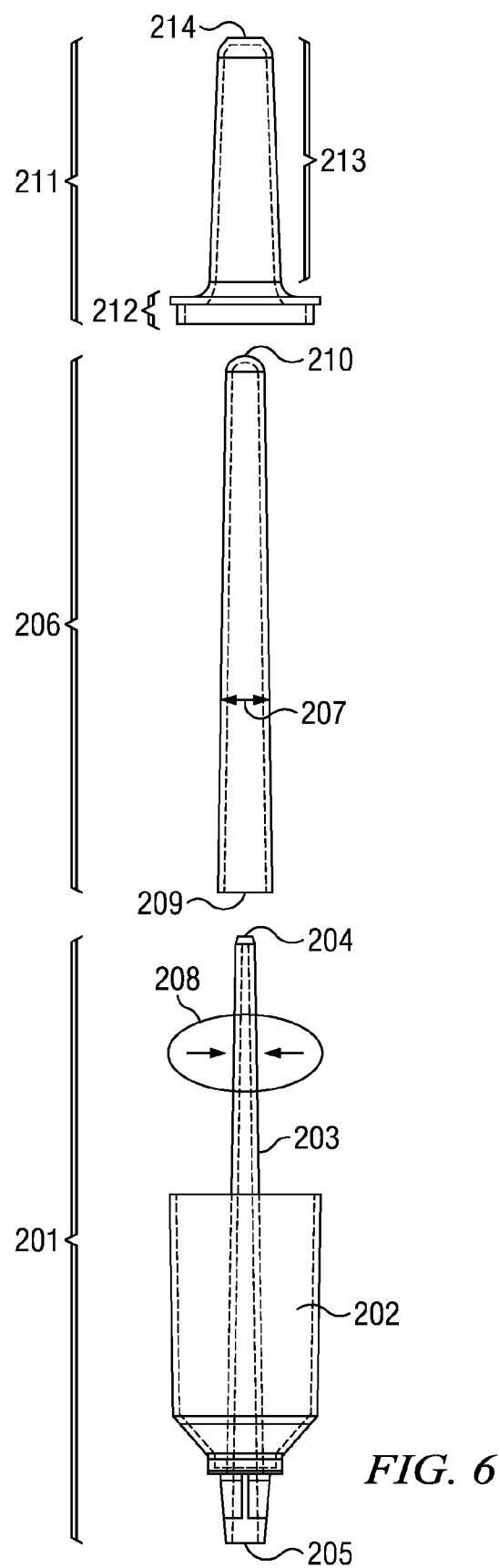
FIG. 6 shows an embodiment of a nasal irrigator in accordance with an embodiment of the present invention.

FIG. 6 shows an embodiment of a nasal irrigator in accordance with the present invention. The nasal irrigator comprises three main components. The first component is the main canister 201, which has a fluid reservoir 202 and an air exit port 203 that extends above the reservoir. In one embodiment, the reservoir 202 holds up to 30 ml of fluid or medication. As shown in FIG. 1, the lower portion of the reservoir is downward sloping to ensure fluid collects at the bottom, which allows maximal uptake of fluid through fluid channels (explained below), thereby minimizing waste.

The air exit port 203 has at least one exit hole 204 at the top sufficient to deliver an airstream that is able to atomize fluid and deliver the aerosol to the whole nasal cavity. In one embodiment, the exit hole 204 is between 0.020" (0.508 mm) and 0.060" (1.524 mm) in diameter and the air exit port has a web-thickness of between 0.030" and 0.200" (0.762 mm-5.08 mm).

The main canister 201 also included an air inlet 205 on the bottom for the admission of pressurized air to create the air stream exiting the air exit port 203.

In one embodiment, the main canister 201 has optional "feet" on the bottom (as shown in FIG. 1) for stability. The length of all components on the nozzle cone is limited so that the nozzle cone or its components do not extend past the feet on the main canister when the device is assembled to enable the device to be placed on a flat surface in an upright or standing position. The canister 201 may also be designed to fit into a standard docking port of an air compressor to enable the device to remain upright in a hands-free situation so as to be filled with the air supply tube attached.

The second main component of the nasal irrigator is an insert 206 that fits over the main canister's air exit port 203. The insert 206 can be permanently attached to the canister 201 or it may be removable. The insert 206 has an aerosol exit 210 that is concentrically aligned with the exit hole 204 of the air outlet 203. A peak or extension on the air exit port 203 may ensure centering of the insert over the air outlet. Similarly, tabs on the insert may be used to center the insert over the air outlet and prevent it from being moved by force. The aerosol exit 210 is slightly larger than the exit hole 204 of the air exit port 203 to enable atomization of fluid in the air stream.

The insert 206 has a tapered inner diameter 207 that is larger than and follows the contours of the outer diameter 208 of the air exit port 203. This difference in diameter creates a space of between 0.0001" (0.00254 mm) and 0.010" (0.254 mm) between the inner surface of the insert 206 and the outer surface of the air exit port 203. This space allows fluid to be drawn from the reservoir 202 through a channel 209 at the base that is sized to control the fluid flow.

The third main component of the nasal irrigator is the cover 211 that mates with the reservoir 202 of the main canister 201 and extends over the insert 206 such that the insert does not contact the nose as the device is inserted into the nasal cavity, thereby ensuring that the hole 210 in the insert 206 and the hole 204 in the air exit port 203 remain concentrically aligned. The cover 211 includes a mating surface 212 that creates a preferably isodiametric connection to the main canister 201 and extends around the nozzle formed by the insert 206 and air exit port 203. The cover 211 extends just above the insert 206 and has its own exit hole 214 designed not to restrict the flow of the aerosol plume. In one embodiment, the cover 211 provides a cross member or other feature that secures the insert 206 to prevent lifting of the insert at the initiation of atomization.

Figure 7:
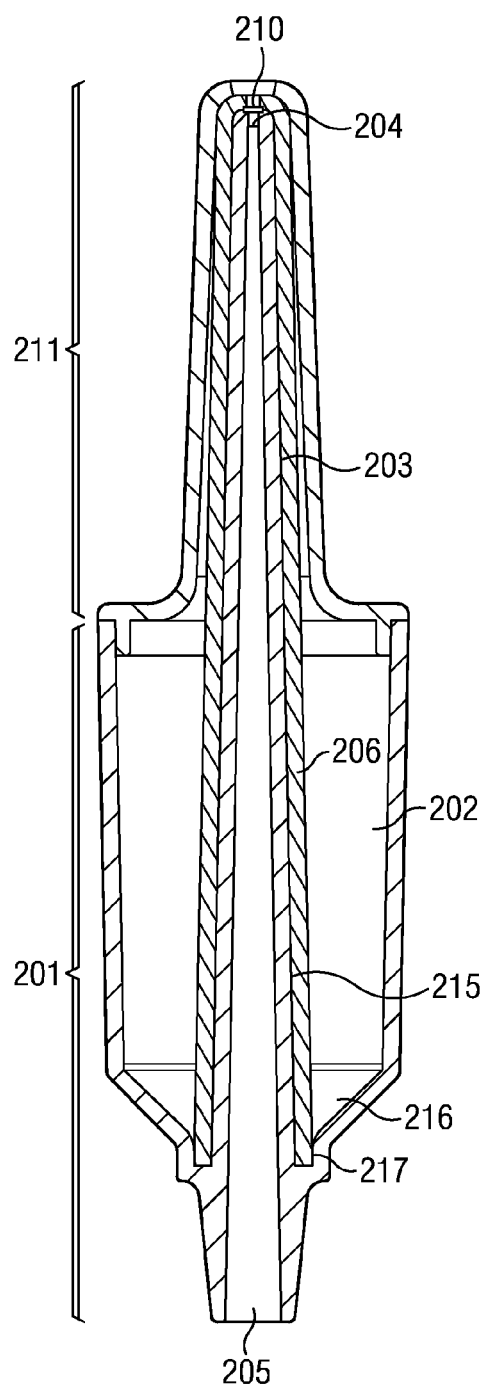
FIG. 7 is a schematic cross sectional view of the assembled nasal irrigator of FIG. 6.

FIG. 7 is a schematic cross section view of the assembled nasal irrigator in accordance with the present invention. This view shows the alignment of the canister 201, insert 206, and cover 211 and the resulting fluid space 215. When fluid is in the reservoir 202 and a pressurized air source is introduced to the system via air inlet 205, a vacuum is created in the space 215 as air exits through outlets 204 and 210. Because the aerosol exit hole 210 in the insert 206 is larger than the exit hole 204 of the air exit port 203, when air is forced through the air exit port 203 at an appropriate volume and speed it creates a venturi effect as the pressurized gas is expelled, thereby drawing fluid in the reservoir 202 up into the space 215 between the insert and air outlet. When the fluid reaches the airstream between the exit holes 204, 210, it is atomized in the airstream to create an aerosol. This aerosol is sufficiently dispersed within the nasal cavity above the inferior turbinate so as to the reach the upper nasal cavity.

The aerosol exit 210 in the insert 206 is small enough to ensure that a mist is created yet large enough to ensure that the hole can be chamfered on the outer side to reduce agglomeration of the mist particles upon exit. The aerosol exit hole 210 is chamfered so that the walls of the exit are angled away from a central axis of the hole such that the angle is greater than that of the aerosol plume. This chamfering reduces agglomeration of particles on the walls of the aerosol exit hole 210, resulting in uniformity of particle size across the resultant aerosol plume.

The base of the insert 206 sits in a groove 217 at the base of the canister 201, ensuring that all fluid is drawn from the bottom of the canister.

The nebulizer components of the present invention can be made from materials such as rigid plastic, glass, metal, ceramic, carbon fiber or other rigid material, an elastomer plastic, or some combination thereof.

Figure 8:
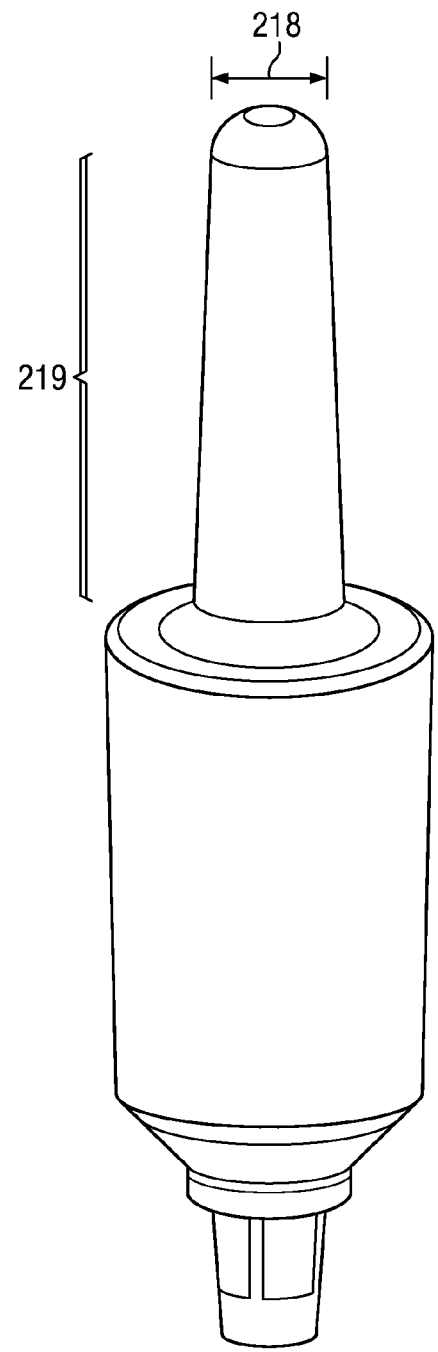
FIG. 8 shows a perspective view of an assembled nasal irrigator in accordance with an embodiment of the present invention.

FIG. 8 shows a perspective view of an assembled nasal irrigator in accordance with the present invention. By maintaining a sufficiently narrow nozzle assembly 218, and a sufficiently long and smooth cover 219, the device can be easily and atraumatically inserted into the nose of the patient so that the nozzle 218 extends to or above the nasal valve. The device is then angled by the user to obtain the best distribution based on the user's anatomy. The mist enters the nasal cavity independent of the patient's breathing.

The nasal irrigator of the present invention may also include a feature that guides the user to angle the spray into the nose to a set angle of between 0 and 90 degrees from the vertical plane of the face (defined as the front of the face from the chin to the forehead). For example, one embodiment of the nasal irrigator includes a setoff that sets a specific angle of 30 degrees from the vertical plane of the face. In another embodiment, the setoff angle is 60 degrees from vertical, and in another embodiment the setoff angle is 45 degrees from vertical. The setoff described above is removable to accommodate various size faces and noses.

The method of nasal irrigation of the present invention uses a variable particle size up to 100 microns under a pressure of 1-15 psi (0.069-1.0345 bar), creating a pressurized airflow that enables the resultant air-mist stream to reach the whole nasal cavity independent of the patient's breathing. The resultant aerosol mist reaches the area of the nasal cavity above the inferior nasal turbinate or chonchae to ensure that the mist reaches the areas of the sinus ostia to clear this area of the nasal cavity and enable the natural mucociliary flow to clear the sinuses.

By adjusting the size of the exit holes 204 and 210, the air-fluid mixture can be calibrated to achieve nasal irrigation within a short period of time, without the need for the fluid to exit the nostrils at the time of irrigation, and with a particle size that is designed to loosen the mucous or to enter the sinus cavities, as desired by the end user. In many applications, ideally a mist of 20 microns is delivered at a rate of 0.5 ml per second.

The aerosol mist itself is typically medicated with at least one, and often two or more therapeutic agents. Possible therapeutic agents for use in the medicated mist, either alone or in combination include antibiotics, antifungal agents, corticosteroids and mucolytic agents. The mist may also be medicated with a neurologically-active agent targeting the central nervous system through the cranial nerves innervating at least a portion of the nasal cavity as well as systemically-active agents.

Figure 11:
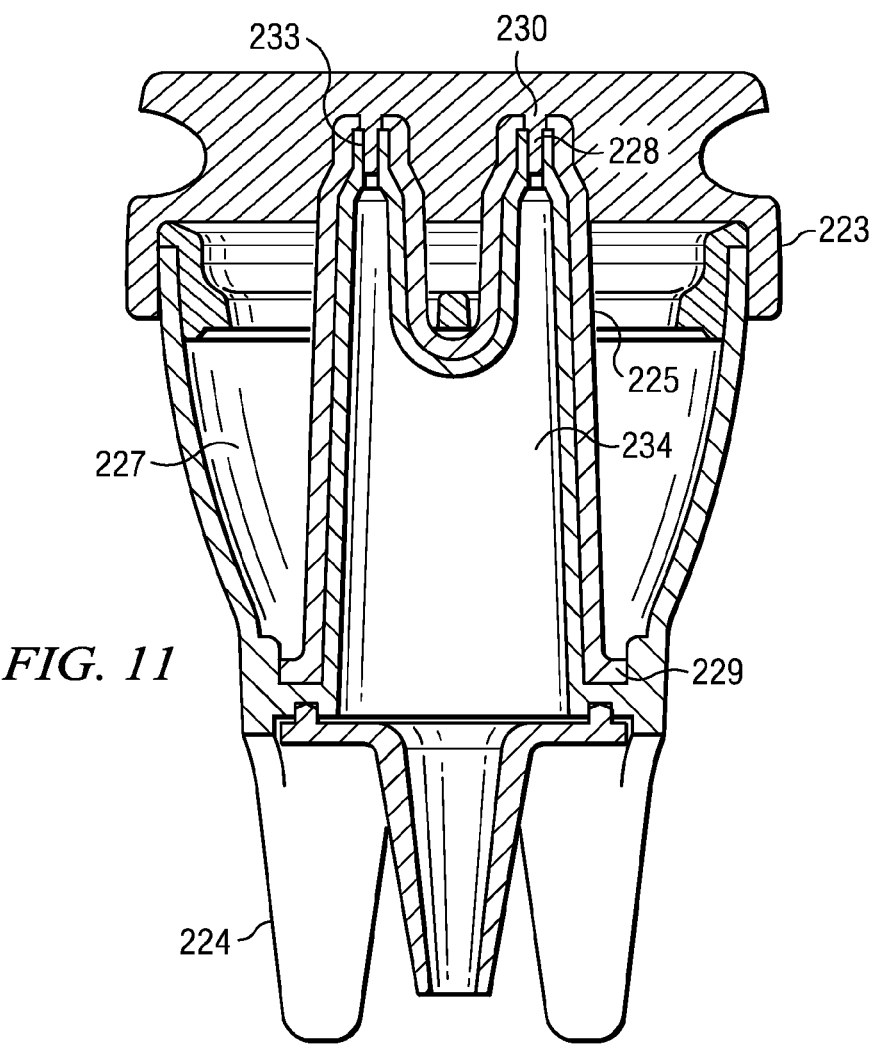
FIG. 11 is a schematic cross sectional view of the assembled nasal nebulizer of FIG. 10.
Figure 12B:
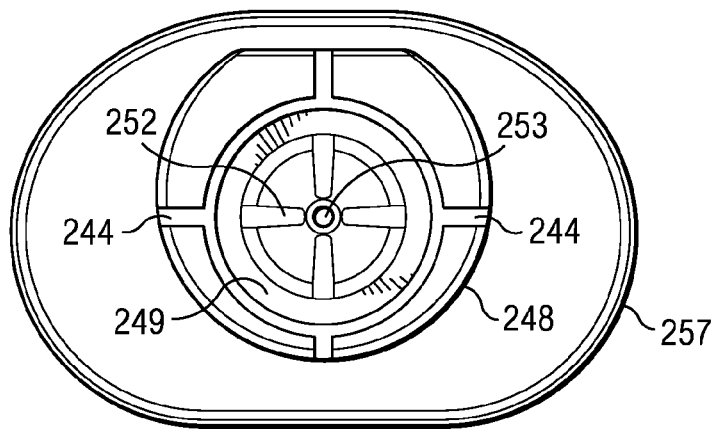
FIG. 12b shows a bottom view of an insert in accordance with an embodiment of the present invention.
Figure 13A:
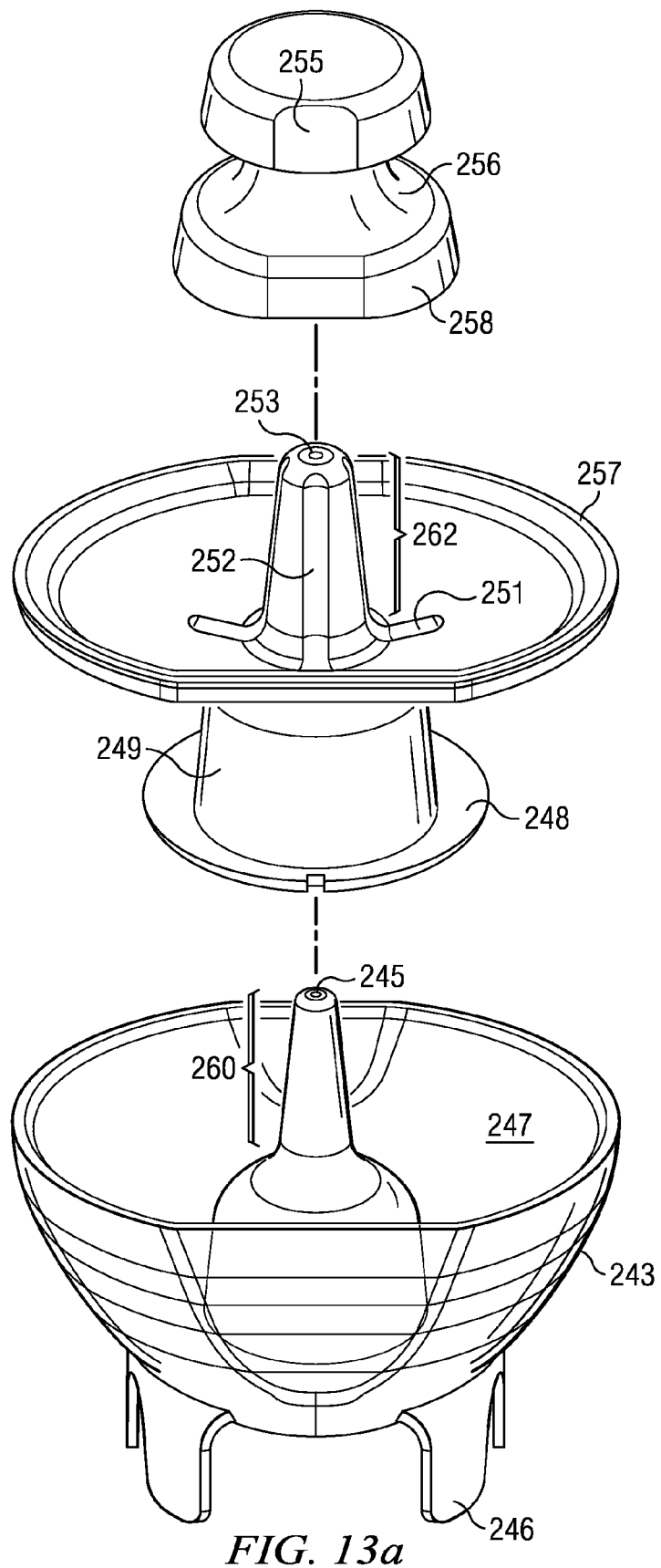
FIG. 13a shows a top perspective exploded view of the nasal nebulizer of FIG. 12.
Figure 13B:
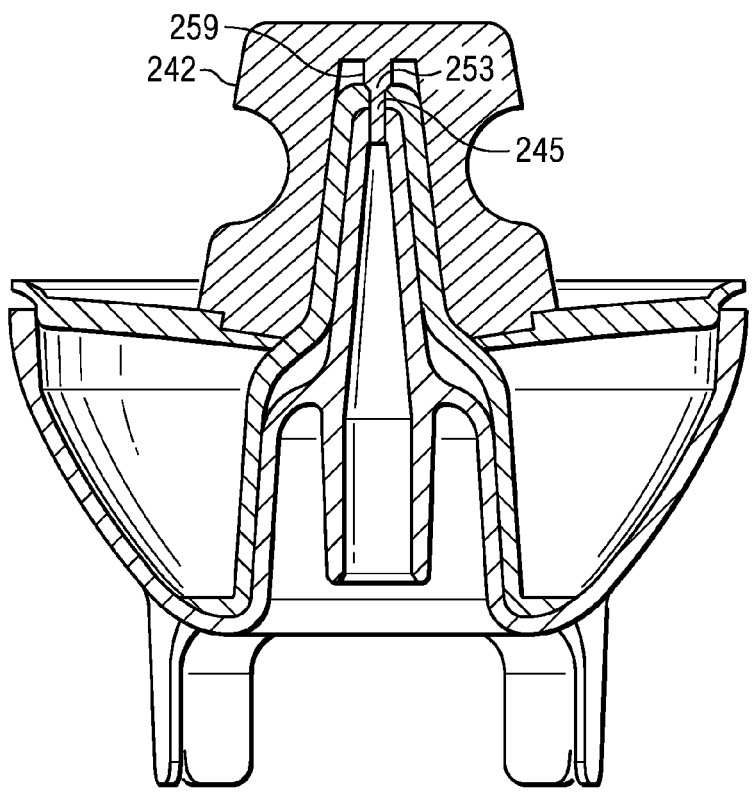
FIG. 13b shows a cross-sectional side view of an assembled nebulizer in accordance with the present invention.
Figure 14:
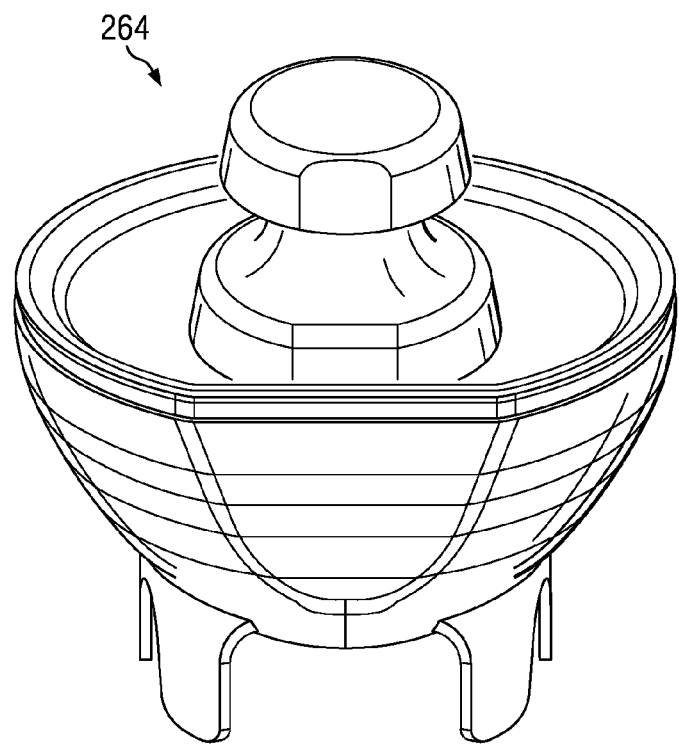
FIG. 14 shows a perspective view of an assembled nasal nebulizer in accordance with the present invention.

FIG. 9a is an exploded view of an improved nasal nebulizer device according to one embodiment of the present invention. The device comprises a main canister 220, an insert 221, and a cap 223. The main canister 220 and the insert 221 comprise many of the same characteristics of the nebulizer described with relation to FIG. 1. The main canister 220 comprises a rim surrounding a reservoir 227, which can hold up to 50 mL of fluid. While the reservoir is depicted as substantially circular, it should be appreciated that the reservoir may comprise any shape. In one embodiment, the reservoir comprises an oval shape. As previously described with respect to FIG. 1, the main canister 220 also comprises an air chamber that terminates into at least one air exit port 228. In one embodiment, as depicted in FIGS. 9-11, the air chamber of the canister terminates into two air exits ports 228 (one for each nostril). In another embodiment, as best depicted in FIGS. 12-14, the air chamber of the canister terminates into only one single air exit port.

As described above with respect to FIG. 1, each air exit port 228 has at least one hole of between 0.020" and 0.060" (0.508 mm-1.524 mm) in diameter and a web-thickness or hole length of between 0.030" and 0.200" (0.762 mm-5.08 mm). In addition, as with the embodiment of FIG. 1, on the bottom of the main canister 220 is a foot section 224 that includes at least one foot for stability and an air inlet (as depicted in FIG. 11) for the admission of pressurized air to create the air stream through air exit ports 228. The foot section 224 enables the canister 220 to remain standing on its own when set on a substantially horizontal surface and is designed to fit into a standard docking port of an air compressor pump to enable the device to remain upright in a hands-free manner so as to remain filled with the air supply tube attached.

The insert 221 comprises a base 229 that fits within the canister 220 and sits just off the bottom of the reservoir 227. In one embodiment, as depicted in FIG. 9, the base 229 is circular. However, the base may comprise any number of shapes so long as it fits within the canister. The insert 221 further comprises a fluid channel 225 that fits over the air exit port 228, said fluid channel 225 comprising a tube portion ending in a common bell housing 234 above the base. In one embodiment, the insert comprises two fluid channels. In another embodiment, described below, the insert comprises one fluid channel.

As best depicted in FIG. 9b, the bottom face of the base 229 of the insert 221 comprises at least one groove 226 that forms a communication channel between the canister and the common bell housing of the insert. The groove 226 extends from the outside of the base to the inside of the insert. The base should comprise at least one groove but may also comprise more than one, as depicted in FIG. 9b. The number of grooves as well as the width and depth of the groove will help regulate the flow of fluid up to the point that the airflow takes over the upper limit of flow. In one embodiment, the grooves may range in width from about 0.005" to about 0.150" (0.127 mm to about 3.81 mm). In one embodiment, the grooves may range in depth from about 0.001" to about 0.050" (0.0254 to about 1.27 mm). The fluid channel 225 is larger in diameter than the air exit port 228, thereby providing a small space between the outer surface of the air exit port 228 and the inner surface of the fluid channel 225 that allows fluid from said reservoir 227 to be drawn through the communication channel and upward between the air exit port 228 and the fluid channel 225 such that the fluid is expelled as a mist in an aerosol plume through an exit hole 230 in the fluid channel due to a venturi effect created by the introduction of pressurized air from the air exit port.

In one aspect, the canister 220 and the insert 221 are preferably affixed together such that the insert 221 and the canister 220 together form an integral piece. As used herein, "affix" relates to a secure attachment between the canister and insert and may include both permanent bonding and temporary bonding, which may only be subsequently manually separated. Preferably, the affixing of the insert and canister will not interfere with or negatively affect the communication channel(s) formed by the grooves in the bottom face of the insert. In one embodiment, the insert 221 is permanently affixed or bonded to the canister 220 at the bottom face of the insert. The bond may be formed by any means known in the art including without limitation use of a solvent bond, glue UV-cured adhesives, mechanical attachment, heat forming, or radiofrequency or ultrasonic welding. In another embodiment, the canister 220 and the insert 221 may mechanically mate together, such as with a friction fit or a snap fit, to form a temporary connection between them that can be subsequently separated by the user as desired.

In yet another embodiment, where the insert comprises two fluid channels, the nasal nebulizer may further comprise a cross bar component 222 having an edge that fits around the rim of the canister. The crossbar component may comprise a single crossbar 232 that extends from one edge of the component 222 to another edge, dividing the component 222 into two substantially equal halves, as depicted in FIG. 9a for example; or it may comprise a crossbar that extends from one edge to one or more other edges at a different locations around the circumference, dividing the enclosed space into multiple areas. In such embodiments, the crossbar component 222 may be permanently affixed or bonded to the rim of the canister 220, thereby affixing the insert 221 to the canister 220. The bond may be formed by any means known in the art including without limitation use of a solvent bond, glue UV-cured adhesives, mechanical attachment, heat forming, or radiofrequency or ultrasonic welding.

Covering the canister 220, insert 221, and optional crossbar component 222 is a cap 223 without holes therethrough. As depicted in FIG. 10, a cap 223 fits over the rim of the canister 220 and covers the tube portion of the insert, plugging the exit hole 230 of the fluid channel 225 and the air exit port 228 to form an airtight, hermetic seal for the nebulizer device, preventing the leakage of the fluid from the reservoir. The cap may further comprise an alignment feature or thumb hold 231 along its outer edge, which may align with a similar alignment feature or thumb hold on the exterior of the canister 220. Thus, the nebulizer in one embodiment allows for sterile or non-sterile drug storage and serves as a carrier for the transport or shipment of medication or irrigation fluid.

FIG. 11 is a cross sectional view of an assembled nasal nebulizer comprising a canister 220, insert 221, optional crossbar component, and cap 223. As best shown here in FIG. 11, the cap 223 may comprise sealing plugs 233 recessed within the cap, which extend through both the exit hole 230 of the fluid channel 225 and the air exit port 228. In one embodiment, the sealing plugs 233 may be comprised of an expandable material, which will expand once removed from the top of the nebulizer device. In another embodiment, the cap may be threaded and include a gasket to form a compression seal. When ready for use, a user can remove the cap and connect an air supply to the air inlet beneath the reservoir.

A method of forming a disposable nasal nebulizer in comprises the steps of providing a canister 220 with an air exit port 228 and a rim surrounding a reservoir 227 for holding fluid; providing an insert 221 with a base 229 that fits within the canister 220, the insert 221 comprising a fluid channel 225 that fits over the air exit port 228, said fluid channel comprising a tube portion ending in a common bell housing 234 above the base, said base comprising at least one groove 226 along its bottom face forming a communication channel between the reservoir 227 of the canister 220 and the common bell housing 234, wherein the fluid channel 225 is larger in diameter than the air exit port 228, thereby providing a small space between the outer surface of the air exit port 228 and the inner surface of the fluid channel 225 that allows fluid from said reservoir 227 to be drawn through the communication channel and upward between the air exit port 228 and fluid channel 225; and affixing the canister 220 together with the insert 221, thereby forming one integral structure.

The providing steps (a) and (b) can comprise the step of manufacturing the canister or the insert, or both the canister and the insert. The manufacturing can be performed by any means known in the art including without limitation molding, forming, shaping or any combination thereof. The providing step (a) may also comprise the step of obtaining the canister from any manufacturer or vendor, for example. Similarly, the providing step (b) may comprise the step of obtaining the insert from any manufacturer or vendor. By way of example, in one embodiment, the insert may be permanently attached to the canister along its base 229. Preferably, the bond would be formed such that the groove 226 remains a communication channel. Thus, the bonding should not substantially block or plug the groove 226. In one embodiment, the insert is bonded or permanently attached along its bottom face to an interior side of the canister. A suitable solvent bond includes, for example, any plastic adhesive including without limitation ABS, acrylic, polystyrene, and polycarbonate solvents such as cyclohexanone. With the insert and canister forming one integral structure, fluid may be inserted into the reservoir 227 and the cap 223 can be placed over the rim of the canister to seal the fluid within the nebulizer device for transport or shipment.

Figure 12A:
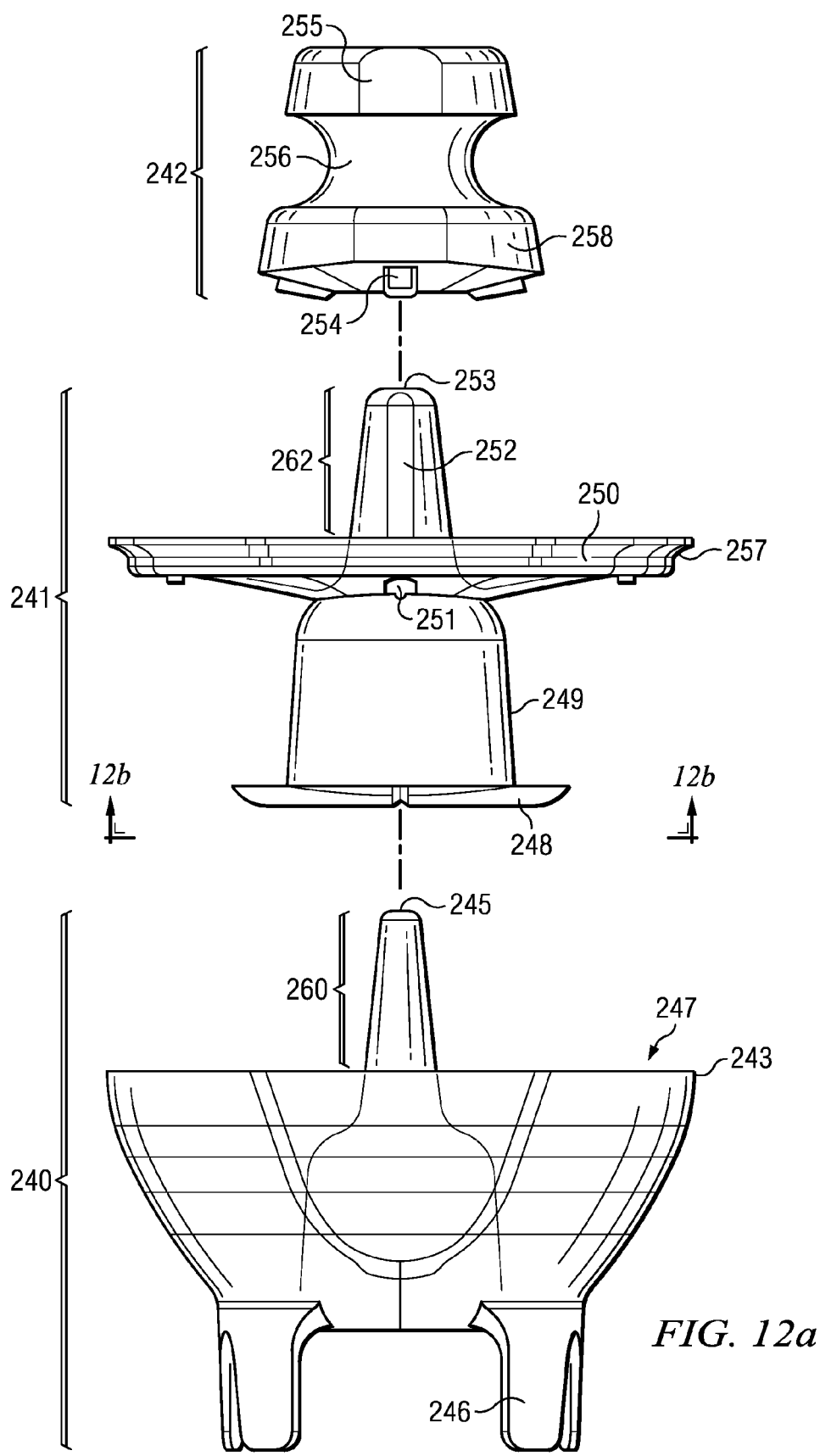
FIG. 12a shows an exploded view of a nasal nebulizer in accordance with an embodiment of the present invention.

FIG. 12a depicts an exploded view of another embodiment of a nasal nebulizer. Similar to the above devices, the nasal nebulizer comprises a main canister 240 with an air exit port 245 and a rim 243 surrounding a reservoir 247 for holding fluid. The air exit port 245 extends beyond the rim 243 of the canister and has at least one exit hole at the top sufficient to deliver an airstream that is able to atomize fluid and deliver an aerosol. The main canister may also comprise the foot section 246 for stability. In addition, if desired, the canister may comprise one or more horizontal marks or lines to indicate specific fluid levels.

FIG. 12b depicts an embodiment of the insert 241 with a base 248 that fits within the main canister 240, wherein the insert has a bottom face with at least one groove 244 to form a communication channel between the canister 240 and the common bell housing 249. In one embodiment, as depicted in FIG. 12b, the groove at the bottom of the insert 241 may extend from the outside edge of the bottom face to a peripheral groove surrounding the opening of the common bell housing. The insert further comprises an extension 250. As depicted in FIGS. 12a and 13a, in one embodiment, the extension 250 protrudes outwardly from the mid-section of the insert 241 above the common bell housing 249. In other embodiments, however, the extension may also extend from another point along the insert, from the common bell housing to any point closer to the exit 253 of the fluid channel. The extension 250 forms a top, or lid, to the canister 240 that mates with the rim 243 of the canister. In one embodiment, the extension comprises a downward concave shape relative to a plane substantially perpendicular to the fluid channel; or, relative to the top surface of the lid. In one embodiment, the extension comprises a two-step diameter 257 to mate with the rim 243. The insert 241 further comprises one or more apertures 251 around the fluid channel, each of the apertures lining up with a vertical groove 252 along the exterior of the fluid channel 262. The groove 252 runs vertically from a point below the exit hole of the fluid channel 253 down to an aperture 251 in the extension 250. During use, the deflected fluid will begin to flow back down the vertical groove 252. The aperture 251 communicates with the inner chamber formed by the mating of the main canister 240 and insert 241. As fluid exits the inner reservoir, a vacuum is created that actually pulls the deflected fluid back into the reservoir 247 through the aperture 251, thereby ensuring maximum usage and minimized waste of the fluid.

The nebulizer further comprises a cap 242 without holes that fits over and inserts into the fluid channel 253 and the air exit port 245 to seal the reservoir from the air exit and fluid exit. The cap comprises an elongated portion 256 to ensure a good fit over the tube portion. Optionally, the cap may comprise a flattened edge 255 to help with alignment with the apertures 251 of the insert 242 and also help with the grasping the cap 242. The bottom portion 258 of the cap mates with a portion of the top face of the extension. Thus, as best depicted in FIG. 12a, the bottom face of the cap 242 is relatively upwardly convex in one embodiment to mate with the downwardly concave extension 250. The cap 242 further comprises one or more projections 254 on its bottom face, which mates with the apertures 251 of the extension. In particular, the projection 254 aligns with and seals the aperture 251 when the cap 242 is placed over the insert 241, as best shown in FIG. 14. Thus, the number of projections 254 on the bottom face of the cap 242 should equal the number of apertures 251 in the insert 250. As best depicted in FIG. 13b, the cap further comprises a sealing plug 259 that projects into and fits within the exit hole of the fluid channel 253 in the insert 241 and the air exit port 245, thereby sealing the nasal nebulizer.

Similar to the embodiments described above with regard to FIGS. 9-11, in order to make a disposable device in accordance with one aspect of the present invention, the canister 240 and the insert 241 are affixed together such that the insert 241 and the canister 240 together form an integral or single piece. In embodiments comprising an extension 250 extending from the insert to the rim of the canister (as depicted in FIGS. 12-13), the extension may form a top that mates with the rim of the canister and the edges of the extension may be permanently affixed to the rim of the canister. Thus, in one embodiment, it is the extension that is permanently affixed to the rim of the canister by way of bonding, for example. In another embodiment, the extension may form a top that mates together with a portion of the canister. A suitable solvent bond includes, for example, any plastic adhesive including without limitation ABS, acrylic, polyacetal, polyethylene, polyester, polypropylene, polystyrene, or polycarbonate solvent, UV-cured adhesive, heat or ultrasonic welding or over molding of materials. Bonding with such materials can be performed by any means known in the art. Having the insert and canister as a single integral piece, fluid may be inserted into the reservoir 247 and the cap 242 can be placed over the exit hole 253 and the aperture(s) 251 of the insert 241 to seal the fluid within the nebulizer device for transport or shipment. The cap sits over the tube portion of the fluid channel and the fluid within the reservoir remains sealed within the nebulizer device until ready for use. FIG. 14 depicts an assembled, sealed device 260 ready for transport.

As with the above embodiments, the orifices of the fluid channels should be positioned relative to the air exits so as to create a venturi effect with the pressurized gas expelled from the gas tubes. Thus, the affixing step should account for this positioning. Because the fluid channel exits in the insert are larger than the air exits, when air is forced through the air exits at an appropriate volume and speed, fluid in the reservoir is drawn up into the space between the insert and air exits ports. When this fluid meets the subsequent airstream it is atomized into particles conducive to deposition in the upper airway.

Figures 15, 16:
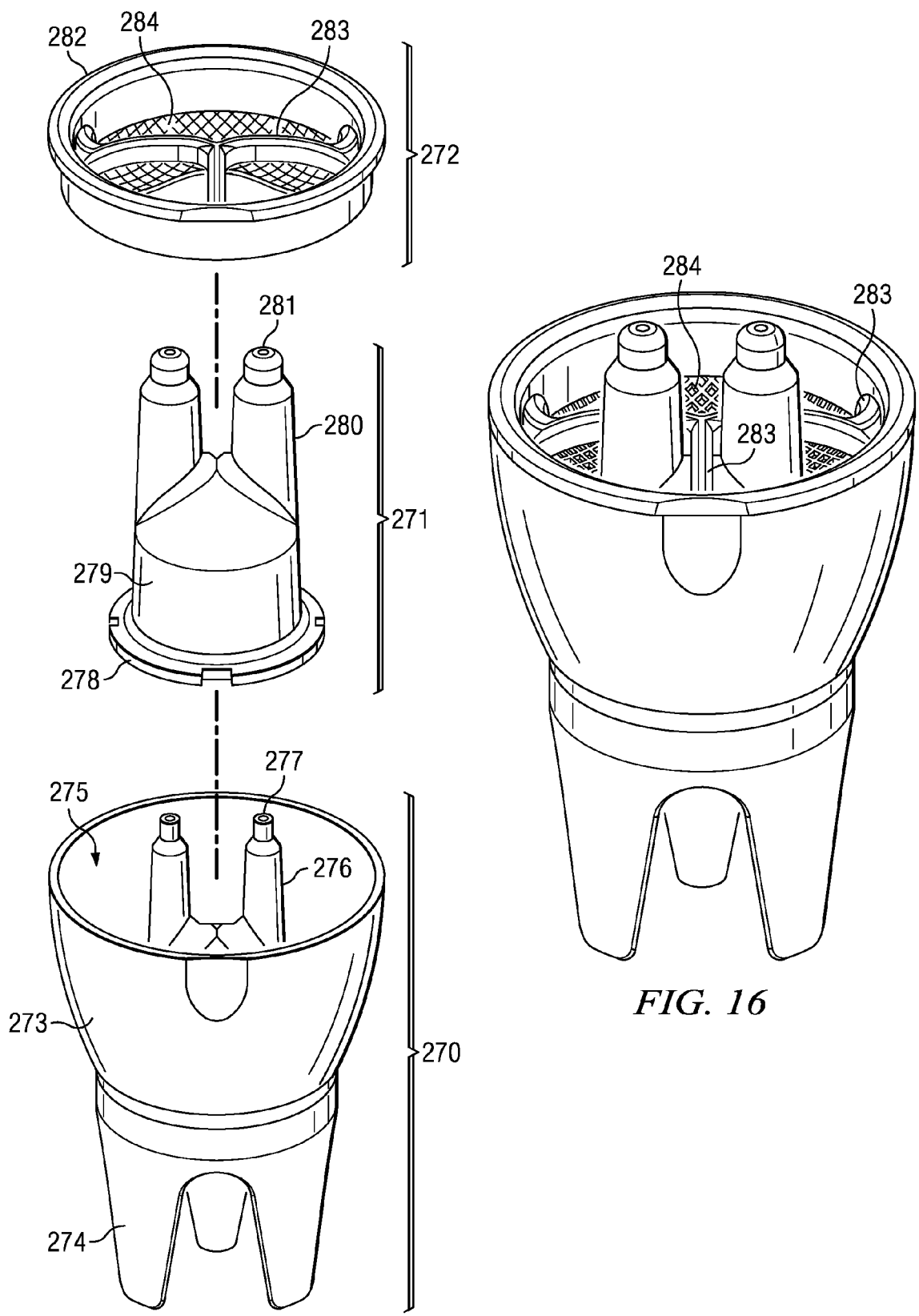
FIG. 15 shows an exploded view of a nasal nebulizer in accordance with an embodiment of the present invention.
FIG. 16 shows a perspective view of an assembled nasal nebulizer in accordance with an embodiment of the present invention.

FIG. 15 is an exploded view of an embodiment of a nasal nebulizer device comprising a canister section 270, an insert 271, and a filter 272. Similar to the above devices, the canister section 270 comprises a canister 273 with reservoir 275 and an air exit port 276 having an exit hole 277. The canister section 270 also comprises one or more feet 274 beneath the canister 273; and the insert 271 comprises a base 278 that fits within the reservoir of the canister and at least one fluid channel 280 with an exit hole 281. As described above, the insert and canister section once formed, shaped, molded or obtained, are affixed to one another.

In one embodiment, the nasal nebulizer device further comprises a filter component 272 that may be inserted over the insert 271. The filter component 272 comprises a filter 284 comprised of a mesh structure with holes small enough to prevent any particulate matter or mucus that runs out of the nose from entering the reservoir 275, while allowing the irrigating or medicating fluid to run back into the reservoir 275 to be re-circulated or re-used. Suitable materials from which to create the filter are plastic, metal, carbon fiber, or other fiber. In embodiments comprising more than one fluid channel, the filter component also comprises a crossbar component 283. In one embodiment, the crossbar 283 is an integral part of the filter component 272. However, it should be understood that the crossbar 283 could also form a separate component, which is detached from the filter, and remains optional.

Figure 17:
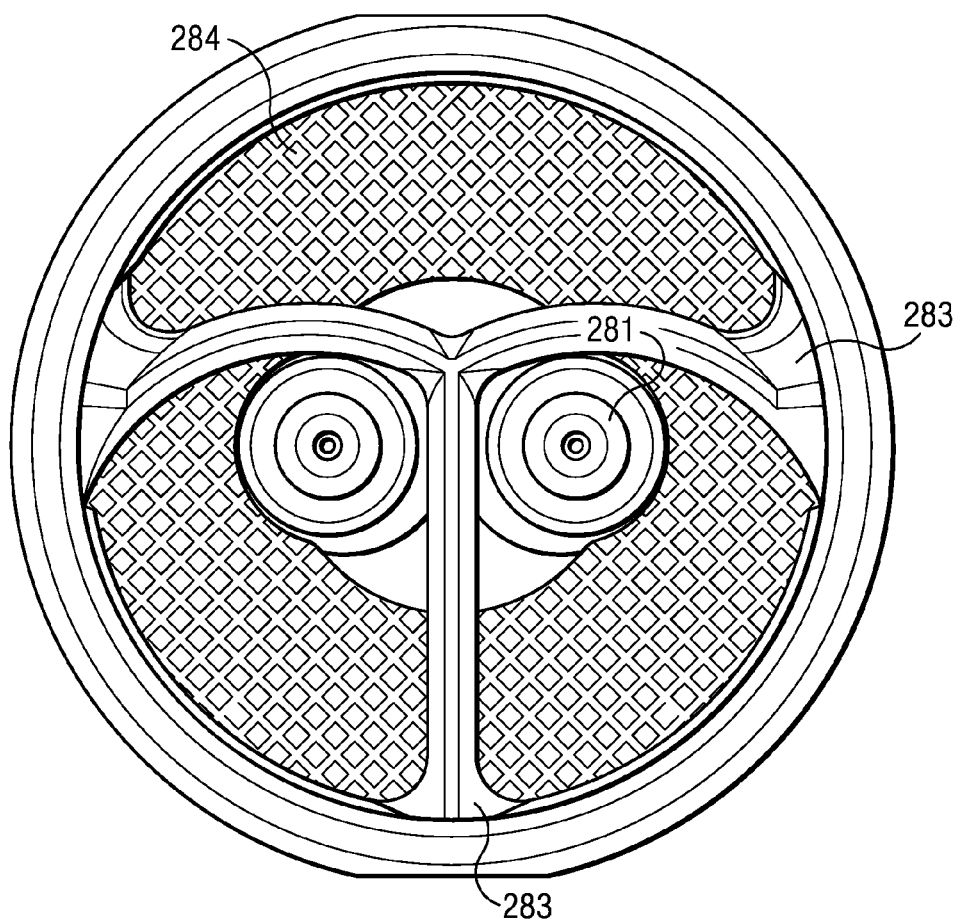
FIG. 17 shows a top view of the nasal nebulizer of FIG. 16.
Figure 18:
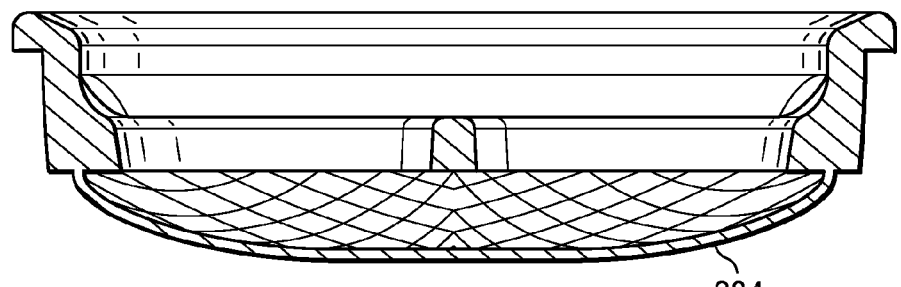
FIG. 18 shows a schematic cross sectional view of a filter in accordance with an embodiment of the present invention.

FIG. 16 is a perspective view of an assembled nebulizer having an insert having two fluid channels 280 and a filter 284 with the optional crossbar 283, wherein the insert is affixed to the canister to form one single integral structure. As described above, in one embodiment, the insert is affixed to the canister by way of bonding. The bonding may comprise the joining of the bottom face of the insert base to the canister or the joining of the periphery of the base to the canister. In one embodiment, the insert may be affixed to the canister by permanently bonding the periphery 282 of the filter to the rim of the insert. As best depicted in FIG. 17, the filter 284 surrounds the tube portion 280 of the insert and extends from the rim of the canister to the tube portion 280, substantially covering the opening of the canister such that when in use, the filter prevents particulate matter from entering the reservoir.

With reference to FIGS. 12 and 13, where the nasal nebulizer comprises an extension, in one embodiment, a filter entirely covers or fits within the apertures 251 in the extension 250 to similarly keep particular matter out of the reservoir and separate from the fluid for re-circulation. The filter may slide over the fluid channel of 241 or may be bonded over or under the apertures 251 or even molded into the insert 241.

Figure 19A:
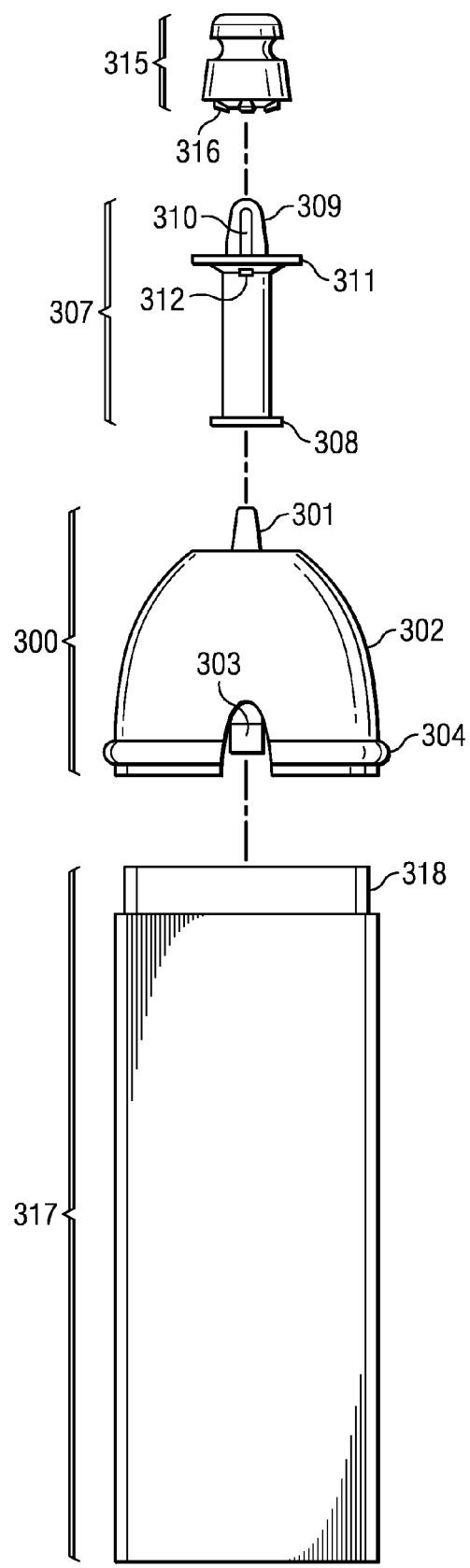
FIG. 19A shows an exploded view of a portable nebulizer according to an embodiment of the present invention.
Figure 19B:
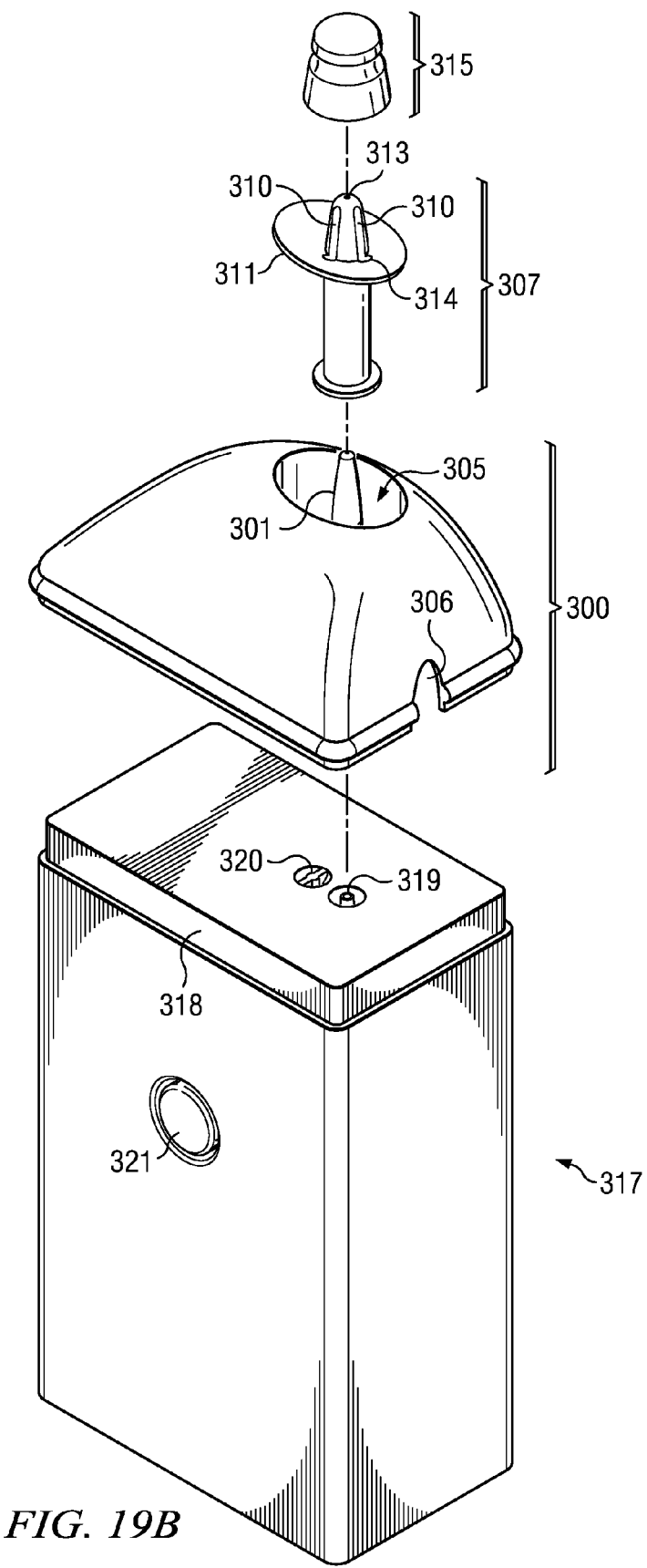
FIG. 19B shows another perspective view of the portable nebulizer shown in FIG. 19A.
Figure 20:
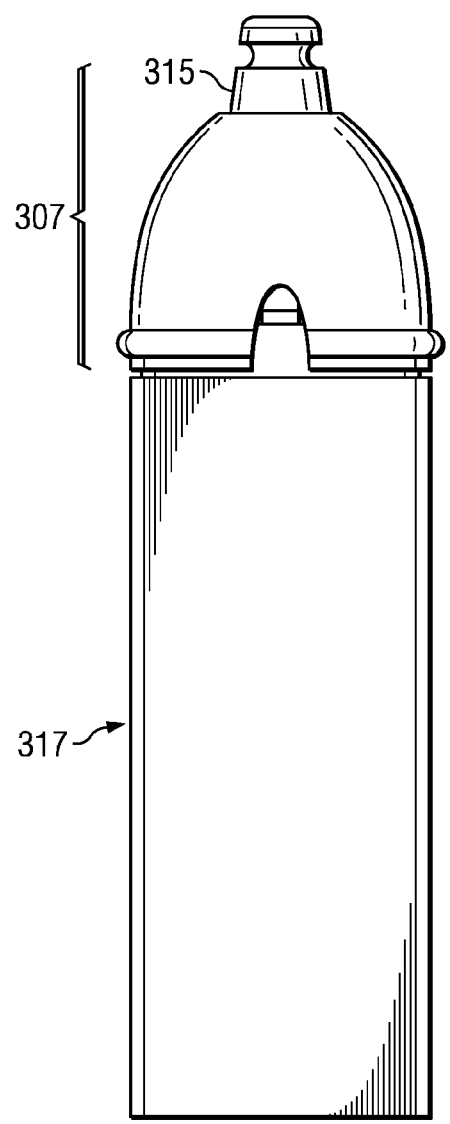
FIG. 20 shows a front perspective view of an assembled portable nebulizer as shown in FIGS. 19A and 19B.
Figure 21A:
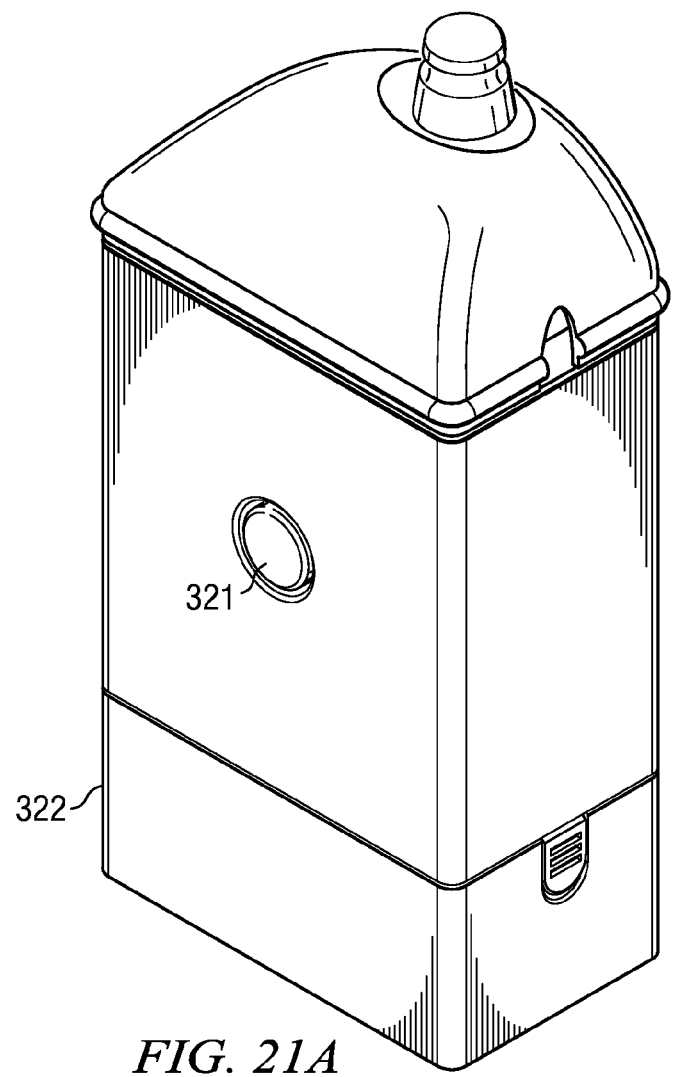
FIG. 21A shows a perspective view of an assembled portable nebulizer according to an embodiment of the present invention.
Figure 21B:
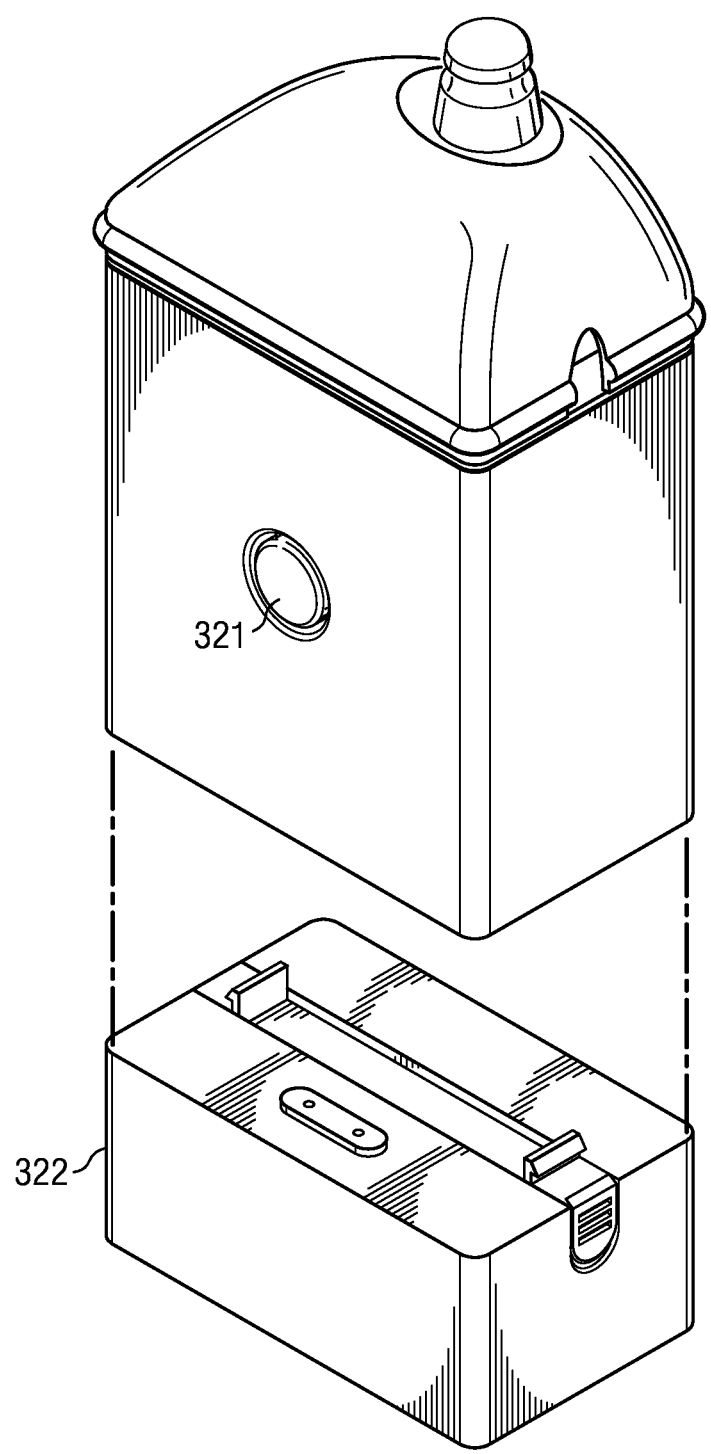
FIG. 21B shows a perspective view of a portable nebulizer as depicted in FIG. 21A.
Figure 22:
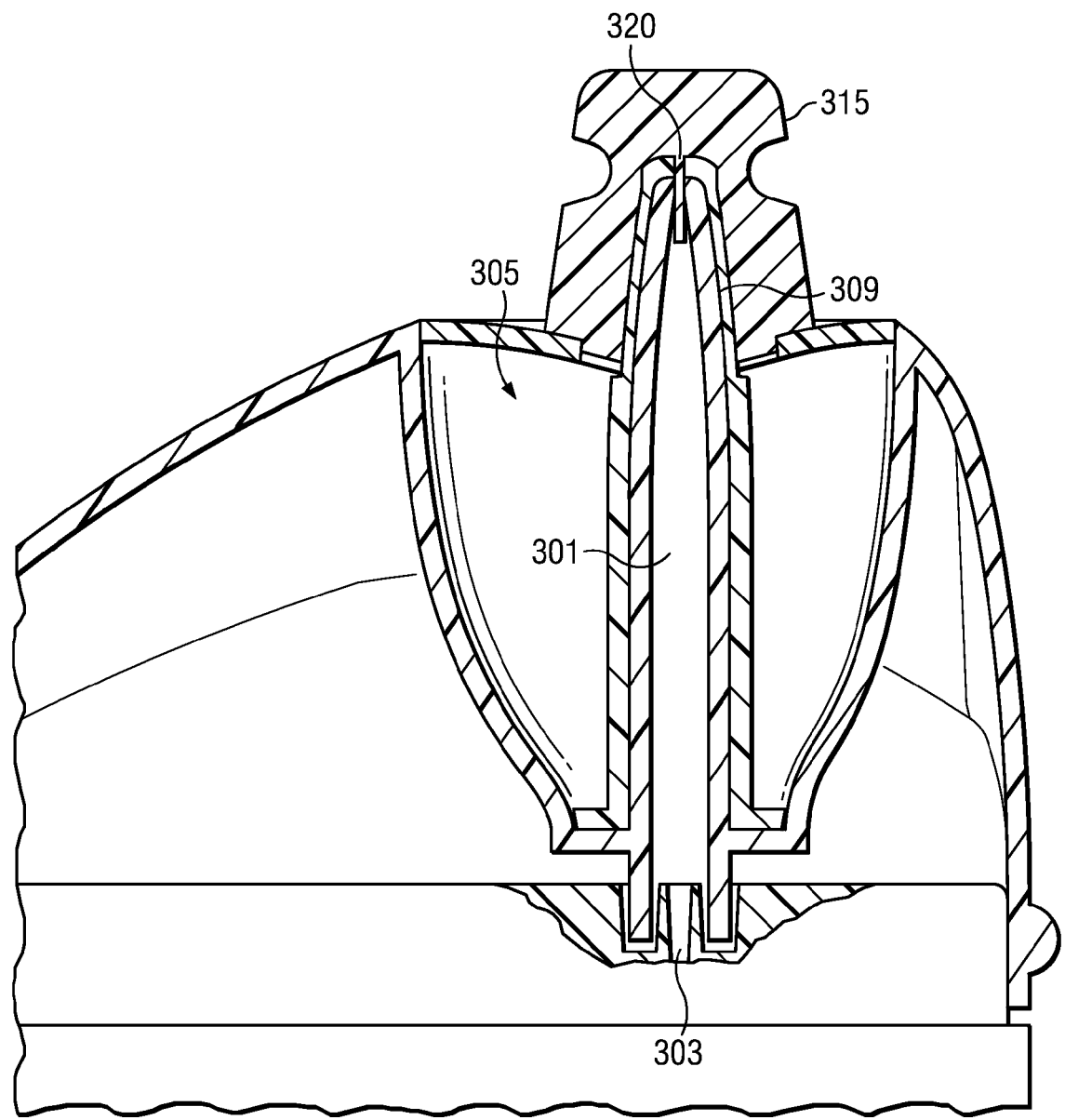
FIG. 22 shows a cross sectional detailed view of a portion of the main canister of an assembled portable nebulizer according to an embodiment of the present invention.
Figure 23:
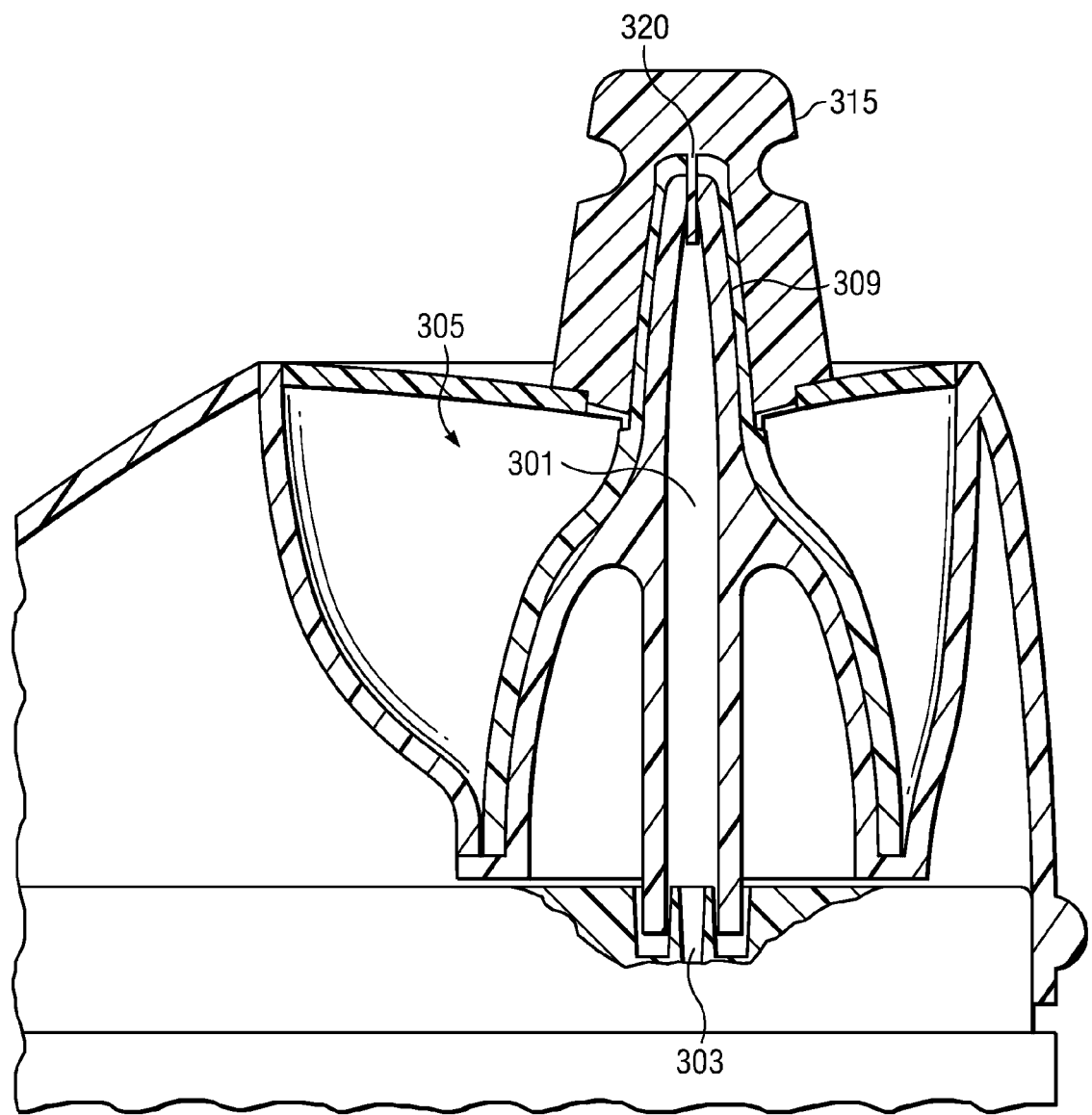
FIG. 23 shows a perspective view of an assembled portable nebulizer according to an alternate embodiment of the present invention.

FIGS. 19A and 19B show an exploded view of a portable nasal nebulizer in accordance with an embodiment of the present invention. The portable nebulizer comprises four sections. The first major section is the main canister 300, which comprises a reservoir 305 for receiving fluid. The main canister 300 further comprises an air exit port 301. As depicted in the figures, the air exit port 301 may extend above the top edge of the main canister 301. However, in alternate embodiments (not shown), the air exit port 301 may be even with or recessed within the edge or portions of the edge of the main canister 300. While the reservoir is depicted as substantially circular, it should be appreciated that the reservoir may comprise any shape. In one embodiment, the reservoir comprises an oval shape. Preferably, the reservoir should be shaped to allow for the receipt of a maximum amount of fluid.

Returning to the embodiment depicted beginning at FIG. 19A, the main canister further comprises a curved wall 302 surrounding the opening to the reservoir 305. The curved wall 302 comprises a convex shape that extends downwardly around the periphery of the opening into a bottom generally rectangular opening configured to mate with a pressurized air supply, as further discussed below. When viewed from below, the main canister 300 thus comprises a generally hollow portion surrounding the reservoir portion 305.

The second major section of the portable nebulizer is the insert 307, which comprises a base 308 that fits within the reservoir section 305 of the canister. As depicted in FIGS. 19A and 19B, the base 308 is circular. However, the base may comprise any number of shapes so long as it fits within the canister. The insert comprises a fluid channel 309 with one end at the bottom of the reservoir 305 and one end that is positioned in the airstream so that the airstream creates a negative pressure in each tube that draws fluid into the airstream where it is atomized. The end positioned in the airstream comprises an exit hole 313. The fluid channel 309 is slightly larger in diameter than the air exit port 301 of the main canister 300, thereby providing a small space (preferably 0.0001" to 0.010" (0.00254-0.254 mm)) between the outer surface of the air exit ports and the inner surface of the fluid channels. This space allows fluid from the reservoir 305 to proceed upward between the air exit port 301 and the fluid channel 301 until being expelled by pressurized air. When the insert 307 is installed in the main canister 300, the orifice 313 of the fluid channel 301 is positioned relative to the air exit 301 so as to create a venturi effect with the pressurized gas. Because the fluid exit in the insert 313 is larger than the air exits 301, when air is forced through the air exits at an appropriate volume and speed, fluid in the reservoir 305 is drawn up into the space between the insert and air exit port. Thus, when this fluid meets the subsequent airstream it is atomized into particles conducive to deposition in the upper airway. The airstream is sufficient to penetrate the nasal cavity above the inferior turbinate so as to deposit the fluid and provide a washing, irrigation, or deposition to the upper reaches the nasal cavity. The fluid channel size may be adjusted to change the particle size of the mist.

The insert 307 may be keyed in at least one location with the reservoir 305 to ensure that the insert does not rotate in relation to the exit port 301 of the main canister 300 and to aid in centering of the insert 307 and its fluid channel 309 on the air exit port 301. In one embodiment, the insert may also include a feature to ensure that it is inserted into the main canister in only one orientation.

At least one channel is located in the bottom of the insert 307 to act as a conduit for fluid from the reservoir 305 to enter the base 308 of the insert. As best depicted above in FIGS. 9*b* and 12*b*, the bottom face of the base 308 of the insert 307 comprises at least one channel or groove that forms a communication channel between the canister and the insert. The groove extends from the outside of the base to the inside of the insert. The base should comprise at least one groove but may also comprise more than one, as depicted in FIG. 9*b*. The number of grooves as well as the width and depth of the groove will help regulate the flow of fluid up to the point that the airflow takes over the upper limit of flow. In one embodiment, the grooves may range in width from about 0.005" to about 0.150" (0.127 mm to about 3.81 mm). In one embodiment, the grooves may range in depth from about 0.001" to about 0.050" (0.0254 to about 1.27 mm).

The canister 300 and the insert 307 may or may not be affixed together to form one integral piece. The bond may be formed by any means known in the art including without limitation use of a solvent bond, glue UV-cured adhesives, mechanical attachment, heat forming, or radiofrequency or ultrasonic welding. Alternatively, the canister and insert may be affixed together via a mechanical interlocking element such as a friction fit or a snap fit to form a temporary connection.

The insert further comprises an extension 311. As depicted in FIGS. 19A and 19B, the extension 311 protrudes outwardly from the insert 307. The extension 311 may extend from any point along the insert to form a top, or lid, to the canister 300. In one embodiment, the extension substantially covers the opening of the reservoir 305. In another embodiment, the extension entirely covers the opening of the reservoir 305. In one embodiment, the extension comprises a downward concave shape relative to a plane substantially perpendicular to the fluid channel; or, relative to the top surface of the lid. In one embodiment, the extension comprises a two-step diameter (not shown) to mate with a rim of the opening. The insert 307 further comprises one or more apertures 314 around the fluid channel, each of the apertures lining up with a vertical groove 310 along the exterior of the fluid channel 309. The groove 310 runs vertically from a point below the exit hole of the fluid channel 309 down to an aperture 314 in the extension 311. During use, the deflected fluid will begin to flow back down the vertical groove 310. The aperture 314 communicates with the inner chamber formed between the main canister 300 and insert 307. As fluid exits the inner reservoir, a vacuum is created that actually pulls the deflected fluid back into the reservoir 305 through the aperture 314, thereby ensuring maximum usage and minimized waste of the fluid.

Another section of the portable nasal nebulizer is a removable cap 315 of the nasal nebulizer. The cap 315 comprises no holes and fits over and substantially covers the fluid channel 309. Optionally, the cap may comprise a flattened edge (as shown above in FIG. 12A) to help with alignment with the apertures 314 of the insert 307 and also help with the grasping the cap 315. The bottom portion of the cap should mate with a portion of the top face of the extension. The cap 315 further comprises one or more projections 312 on its bottom face, which mates with the apertures 314 of the extension. The number of projections 312 on the bottom face of the cap 315 should equal the number of apertures 314 in the insert 307. As best depicted in FIG. 22, the cap comprises a projection or sealing plug 320 that projects into and fits within the exit hole 313 of the fluid channel and extending into the air exit port 301 of the canister to seal the reservoir from the air exit port and fluid channel exit when the cap is placed over the insert.

A fourth section of the portable nasal nebulizer is a handheld pressurized air supply source 317 onto which the main canister 300 fits. Preferably, the pressurized air supply source is a handheld air compressor. As shown in FIG. 19B, the air supply source comprises an air outlet 319, which connects with the air inlet 303 of the main canister. In one embodiment, the canister snap fits onto the pressurized air supply source 317 to form an airtight seal between the air inlet 303 and the air outlet 319. In one embodiment, the airtight seal may comprise an O-ring or soft plastic portion between the air inlet 303 and the air outlet 319 (not shown). An air input 320 supplies air to the pressurized air supply source 317 and may comprise a filter to keep out foreign materials. In order to accommodate for the air input 320, the main canister 300 comprises an air vent 306, which allows air into the air input 320 without interrupting the airtight seal between the canister 300 and air supply source 317. The bottom rim 304 surrounding the generally rectangular bottom of the main canister 300 is fashioned to fit onto the pressured air supply source 317 such that no wiring or connecting tubing is required. Thus, unlike previous embodiments, a foot section at the bottom of the main canister is not necessary in order to stabilize the canister on a substantially flat surface. Instead, the pressurized air supply connects directly and immediately with the main canister.

While the pressurized air supply source 317 is depicted as having a generally rectangular shape, the source 317 may comprise any shape so long as it remains portable and capable of directly attaching to the main canister without the use of tubing. In one embodiment, the pressurized air supply source 317 is substantially rectangular. Preferably, the pressurized air supply source comprises an ergonomic shape to increase user comfort. For example, the air supply source 317 may comprise a grasping or gripping portion having a shape that corresponds to a palm of a hand of the user. The gripping portion may be on one side of the air supply source, with a second opposing side substantially flat; or it may comprise curves substantially around the entire periphery of the air supply source such that user may hold the portable device lengthwise with his or her hand around substantially the entire pressurized air supply source 317. In one embodiment, the air supply source 317 comprises an ergonomic grasping portion. In another embodiment, the pressurized air supply source 317 is substantially rectangular with curves and features that make it easy to hold in the hand. In order to allow for portability of the nebulizer device, the pressurized air supply should generally be small enough to easily carry or transport. In one embodiment, the pressurized air supply source comprises a ratio of width:length:depth of about 2.5:3:1. In another embodiment, the pressurized air supply source comprises a ratio of width:length:depth of about 9:15:5. In one embodiment, the pressurized air supply source comprises a ratio of width:length:depth of between about 2.5:3:1 to about 9:15:5. By way of example, in one embodiment, the length may be about 15.5 cm, the width may be about 9.2 cm, and the depth may be about 5.7 cm. It should be recognized that any number of sizes and dimensions is possible while maintaining portability.

The pressurized air supply source 317 may employ an AC/DC power supply. The source 317 is DC-operated and may include a rechargeable internal battery or an external, detachable battery for easy exchange of depleted batteries. The source 317 may further be operated using a power switch 321 capable of turning on the air supply. The switch 321 may be an intermittent switch conveniently located on the air supply source 317 such that a user may conveniently reach it with one of his or her fingers. In one embodiment, the air supply source 317 may also comprise an indicator for the level of charge on the battery (not depicted) or a timer that beeps at timed intervals to deliver medication evenly between nostrils (not depicted). As described above, the pressurized air has a pressure of 0.069-1.035 bar and an airflow rate of 1-12 liters per minute, producing a fluid delivery rate of 1-20 ml per minute.

FIG. 20 shows a front perspective view of an assembled portable nebulizer as shown in FIGS. 19A and 19B, with the removable cap positioned over the device. Thus, when fully assembled with the cap in place, the portable nebulizer device is completely self-contained, prohibiting any leakage of fluids. As depicted in FIGS. 19A and 19B, in one embodiment, the pressurized air supply source 317 comprises an internal battery, which may or may not be rechargeable. FIG. 21A shows a perspective view of an assembled portable nebulizer in another embodiment, with a detachable battery compartment 322 for one or more batteries which may or may not be rechargeable. In this embodiment, the battery compartment may detach from a portion of the pressurized air device by way of a switch element. FIG. 21B shows a perspective view of a portable nebulizer as depicted in FIG. 21A, with the battery compartment 322 detached from the air supply source 317.

FIG. 22 shows a cross sectional detailed view of the main canister 300, insert 307 and cap 315 portions in an assembled portable nebulizer according to one embodiment of the present invention. As best depicted here, the air exit port 301 and fluid channel 309 form two overlapping, concentric, tapered tubed having the requisite gap or space, as described above, between them in order to allow for the venturi effect. When connected to the pressurized air supply source 317, the air inlet of the main canister plugs directly the supply source or air compressor by way of its air outlet. An alternate embodiment depicted in FIG. 23 shows that the air exit port 301 and the fluid channel 309 may also include a common bell housing as with previous embodiments.

By way of example, a portable nasal nebulizer device as described herein may be comprised of ABS, Polycarbonate, glass, stainless steel, styrolene, styrene-butadiene copolymer, or any other plastics appropriate for medical device use, and any combination thereof. The device may further be comprised of an antimicrobial compound in some embodiments.

The invention illustratively disclosed herein suitably may be practiced in the absence of any element, which is not specifically disclosed herein. It should also be notes that the invention is not limited to human use, but may also be used with any number of mammals including without limitation equine, canine, feline, non-human primate, rodent, bovine, and porcine.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated. It will be understood by one of ordinary skill in the art that numerous variations will be possible to the disclosed embodiments without going outside the scope of the invention as disclosed in the claims.

I claim:

1. A portable nasal nebulizer, comprising:

(a) a main canister comprising at least one air exit port, wherein the air exit port extends beyond a rim of the canister; and (b) an insert with a base that fits within the canister, wherein the insert comprises at least one fluid channel that fits over the air exit port, and further wherein the fluid channel is larger in diameter than the air exit port, thereby providing a small space between the outer surface of the air exit port and the inner surface of the fluid channel; and (c) a pressurized air supply source contiguously attached without tubing to the canister for introducing pressurized air through the air exit port such that the fluid is expelled as a mist through an exit hole in the fluid channel, wherein the insert comprises an extension protruding outwardly to the canister, wherein the fluid channel comprises a groove extending vertically along the exterior of the fluid channel to an aperture in the extension, said aperture creating a channel to the canister.

2. The portable nasal nebulizer of claim 1 wherein said main canister fits onto the pressurized air supply source.

3. The portable nasal nebulizer of claim 1 wherein said pressurized air supply source attaches directly to an air inlet of the main canister.

4. The portable nasal nebulizer of claim 1 wherein said pressurized air supply source comprises an air outlet that connects directly to an air inlet of the main canister.

5. The portable nasal nebulizer of claim 1 wherein said base comprises at least one groove along its bottom face forming a communication channel between the canister and the fluid channel.

6. The portable nasal nebulizer of claim 1 comprising a cap without holes therethrough that substantially covers the fluid channel of the insert, said cap plugging the exit hole of the fluid channel and the exit port.

7. The portable nasal nebulizer of claim 1 wherein said pressurized air supply source is an air compressor.

8. The portable nasal nebulizer of claim 1 pressurized air supply source comprises a battery source.

9. The portable nasal nebulizer of claim 8 wherein said battery source is internal.

10. The portable nasal nebulizer of claim 8 wherein said battery source is detachable.

11. The portable nasal nebulizer of claim 1 wherein said pressurized air supply source comprises a rechargeable battery.

12. The portable nasal nebulizer of claim 1 wherein said extension forming a lid over a portion of the canister.

13. The portable nasal nebulizer of claim 12 wherein said aperture creating said channel to the canister allows for a vacuum to pull in air and deflected fluid into the canister as the mist exits.

14. The portable nasal nebulizer of claim 12 comprising a cap without holes therethrough, said cap comprising a sealing plug for sealing the air exit port and the fluid channel of the insert and further wherein said cap comprises a projection that fits within an aperture of the extension, thereby sealing the aperture.

15. The portable nasal nebulizer of claim 12 wherein the lid is downwardly concave.

16. The portable nasal nebulizer of claim 12 wherein the extension comprises a two-step circumference.

17. The portable nasal nebulizer of claim 1 wherein said pressurized air supply source comprises a ratio of width:length:depth of about 2.5:3:1.

18. The portable nasal nebulizer of claim 1 wherein said pressurized air supply source comprises an ergonomic shape to increase user comfort.

\* \* \* \* \*